(12) United States Patent
Heneghan et al.

(10) Patent No.: US 11,207,182 B2
(45) Date of Patent: Dec. 28, 2021

(54) HEART VALVE THERAPEUTIC DEVICE

(71) Applicant: The Provost, Fellows, Foundation Scholars, And The Other Members Of Board, Of The College Of The Holy And Undivided Trinity Of Queen Elizabeth Near Dublin (TCD), Dublin (IE)

(72) Inventors: Paul Heneghan, Raheny (IE); Bruce Murphy, Dublin (IE); Lucy O'Keeffe, Dublin (IE); Martin Quinn, Blackrock (IE); Conor Quinn, Malahide (IE)

(73) Assignee: The Provost Fellows, Foundation Scholars and the Other Members of Board, of the College of the Holy and Undivided Trinity of Queen Elizabeth, Near Dublin (TCD), Dublin (IE)

( * ) Notice: Subject to any disclaimer, the term of this patent is extended or adjusted under 35 U.S.C. 154(b) by 0 days.

(21) Appl. No.: 17/205,813

(22) Filed: Mar. 18, 2021

(65) Prior Publication Data

US 2021/0220123 A1    Jul. 22, 2021

Related U.S. Application Data

(63) Continuation of application No. 16/943,621, filed on Jul. 30, 2020, now Pat. No. 10,952,854, which is a (Continued)

(30) Foreign Application Priority Data

Feb. 9, 2018  (EP) .................................... 18156125
Sep. 4, 2018  (EP) .................................... 18192480

(51) Int. Cl.
*A61F 2/24*   (2006.01)

(52) U.S. Cl.
CPC ............ *A61F 2/246* (2013.01); *A61F 2/2418* (2013.01); *A61F 2/2466* (2013.01); (Continued)

(58) Field of Classification Search
CPC .............................. A61F 2/246; A61F 2/2418
See application file for complete search history.

(56) References Cited

U.S. PATENT DOCUMENTS 2,684,069 A   7/1954  Shearman et al.
3,689,942 A   9/1972  Rapp
(Continued)

FOREIGN PATENT DOCUMENTS

AU    2016200392 B2   12/2017
CA       2705942 A1    5/2009
(Continued)

OTHER PUBLICATIONS

Berger et al., Comparison of results and complications of surgical and Amplatzer device closure of atrial septal defects, J. *Thorac. Cardiovasc. Surg.*, 118(4):674-8 (1999).
(Continued)

*Primary Examiner* — Suba Ganesan
(74) *Attorney, Agent, or Firm* — Eversheds Sutherland (US) LLP; Christopher C. Bolten; Albert K. Heng

(57) ABSTRACT

A heart valve therapeutic device (1) comprises a coaptation assist valve (20) comprising a conduit (2) with an outer surface (3) for coaption with the native leaflets, and a prosthetic flow valve (5) mounted within the conduit (2) to allow one-way flow through the conduit (2). Support for the coaptation assist valve (20) is provided by a support (10) for positioning the conduit (2) across the native leaflets, and connectors (15) attaching the conduit (2) to the support (10).

29 Claims, 26 Drawing Sheets

Related U.S. Application Data continuation of application No. PCT/EP2019/053038, filed on Feb. 7, 2019.

(52) U.S. Cl.
CPC .... *A61F 2/2487* (2013.01); *A61F 2220/0008* (2013.01); *A61F 2230/0065* (2013.01)

(56) References Cited

U.S. PATENT DOCUMENTS

| | | |
|---|---|---|
| 3,746,003 A | 7/1973 | Blake et al. |
| 5,509,428 A | 4/1996 | Dunlop |
| 5,792,179 A | 8/1998 | Sideris |
| 6,168,614 B1 | 1/2001 | Andersen et al. |
| 6,332,893 B1 | 12/2001 | Mortier et al. |
| 6,461,366 B1 | 10/2002 | Seguin |
| 6,527,800 B1 | 3/2003 | McGuckin, Jr. et al. |
| 6,540,782 B1 | 4/2003 | Snyders |
| 6,582,462 B1 | 6/2003 | Andersen et al. |
| 6,629,534 B1 | 10/2003 | St. Goar et al. |
| 6,752,813 B2 | 6/2004 | Goldfarb et al. |
| 6,764,510 B2 | 7/2004 | Vidlund et al. |
| 6,821,297 B2 | 11/2004 | Snyders |
| 6,893,459 B1 | 5/2005 | Macoviak |
| 6,955,689 B2 | 10/2005 | Ryan et al. |
| 7,077,862 B2 | 7/2006 | Vidlund et al. |
| 7,678,145 B2 | 3/2010 | Vidlund et al. |
| 7,704,277 B2 | 4/2010 | Zakay et al. |
| 7,785,366 B2 | 8/2010 | Maurer et al. |
| 7,854,762 B2 | 12/2010 | Speziali et al. |
| 7,901,454 B2 | 3/2011 | Kapadia et al. |
| 8,070,805 B2 | 12/2011 | Vidlund et al. |
| 8,216,303 B2 | 7/2012 | Navia |
| 8,449,606 B2 | 5/2013 | Eliasen et al. |
| 8,460,370 B2 | 6/2013 | Zakay et al. |
| 8,470,028 B2 | 6/2013 | Thornton et al. |
| 8,475,525 B2 | 7/2013 | Maisano et al. |
| 8,480,730 B2 | 7/2013 | Maurer et al. |
| 8,486,136 B2 | 7/2013 | Maurer et al. |
| 8,506,624 B2 | 8/2013 | Vidlund et al. |
| 8,579,967 B2 | 11/2013 | Webler et al. |
| 8,758,432 B2 | 6/2014 | Solem |
| 8,888,844 B2 | 11/2014 | Eliasen et al. |
| 8,894,705 B2 | 11/2014 | Eliasen et al. |
| 8,923,973 B2 | 12/2014 | Gross |
| 8,932,348 B2 | 1/2015 | Solem et al. |
| 8,961,596 B2 | 2/2015 | Maisano et al. |
| 8,968,395 B2 | 3/2015 | Hauser et al. |
| 8,979,922 B2 | 3/2015 | Jayasinghe et al. |
| 8,992,605 B2 | 3/2015 | Zakai et al. |
| 9,005,279 B2 | 4/2015 | Gabbay |
| 9,011,523 B2 | 4/2015 | Seguin |
| 9,132,007 B2 | 9/2015 | Menk et al. |
| 9,161,837 B2 | 10/2015 | Kapadia |
| 9,232,998 B2 | 1/2016 | Wilson et al. |
| 9,232,999 B2 | 1/2016 | Maurer et al. |
| 9,289,297 B2 | 3/2016 | Wilson et al. |
| 9,358,112 B2 | 6/2016 | Hlavka et al. |
| 9,370,424 B2 | 6/2016 | Call et al. |
| 9,414,918 B2 | 8/2016 | Chau et al. |
| 9,474,605 B2 | 10/2016 | Rowe et al. |
| 9,498,330 B2 | 11/2016 | Solem |
| 9,510,946 B2 | 12/2016 | Chau et al. |
| 9,545,305 B2 | 1/2017 | Wilson et al. |
| 9,579,199 B2 | 2/2017 | Hauser et al. |
| 9,629,720 B2 | 4/2017 | Nguyen et al. |
| 9,636,223 B2 | 5/2017 | Khalil et al. |
| 9,763,782 B2 | 9/2017 | Solem |
| 9,827,101 B2 | 11/2017 | Solem et al. |
| 10,383,729 B2 | 8/2019 | Quinn |
| 10,682,231 B2 | 6/2020 | Quinn |
| 2002/0103532 A1 | 8/2002 | Langberg et al. |
| 2003/0105520 A1 | 6/2003 | Alferness et al. |
| 2004/0059351 A1 | 3/2004 | Eigler et al. |
| 2004/0127981 A1 | 7/2004 | Rahdert et al. |
| 2004/0138744 A1 | 7/2004 | Lashinski et al. |
| 2004/0153146 A1 | 8/2004 | Lashinski et al. |
| 2004/0210307 A1 | 10/2004 | Khairkhahan |
| 2004/0225354 A1* | 11/2004 | Allen .................. A61F 2/2412 623/2.11 |
| 2004/0243229 A1 | 12/2004 | Vidlund et al. |
| 2005/0033446 A1 | 2/2005 | Deem et al. |
| 2005/0075723 A1 | 4/2005 | Schroeder et al. |
| 2005/0107810 A1 | 5/2005 | Morales et al. |
| 2005/0107871 A1 | 5/2005 | Realyvasquez et al. |
| 2005/0187616 A1 | 8/2005 | Realyvasquez |
| 2005/0222488 A1 | 10/2005 | Chang et al. |
| 2005/0228495 A1 | 10/2005 | Macoviak |
| 2006/0058871 A1 | 3/2006 | Zakay et al. |
| 2006/0178700 A1 | 8/2006 | Quinn |
| 2006/0193899 A1 | 8/2006 | Sawhney |
| 2006/0241745 A1 | 10/2006 | Solem |
| 2007/0093890 A1 | 4/2007 | Eliasen et al. |
| 2007/0185571 A1 | 8/2007 | Kapadia et al. |
| 2007/0198082 A1 | 8/2007 | Kapadia et al. |
| 2007/0232992 A1 | 10/2007 | Kutsko et al. |
| 2007/0255399 A1 | 11/2007 | Eliasen et al. |
| 2007/0265700 A1* | 11/2007 | Eliasen .................. A61F 2/246 623/2.1 |
| 2008/0033541 A1 | 2/2008 | Gelbart et al. |
| 2008/0243245 A1 | 10/2008 | Thambar et al. |
| 2009/0076600 A1 | 3/2009 | Quinn |
| 2009/0149949 A1 | 6/2009 | Quinn |
| 2009/0240326 A1 | 9/2009 | Wilson et al. |
| 2010/0185276 A1 | 7/2010 | Vidlund et al. |
| 2010/0217382 A1 | 8/2010 | Chau et al. |
| 2010/0262233 A1 | 10/2010 | He |
| 2010/0298929 A1 | 11/2010 | Thornton et al. |
| 2010/0298930 A1 | 11/2010 | Orlov |
| 2011/0022164 A1 | 1/2011 | Quinn et al. |
| 2011/0060407 A1 | 3/2011 | Ketai et al. |
| 2011/0112632 A1 | 5/2011 | Chau et al. |
| 2011/0224784 A1 | 9/2011 | Quinn |
| 2011/0257721 A1 | 10/2011 | Tabor |
| 2012/0010700 A1 | 1/2012 | Spenser |
| 2013/0018459 A1 | 1/2013 | Maisano et al. |
| 2013/0090728 A1 | 4/2013 | Solem |
| 2013/0172978 A1 | 7/2013 | Vidlund et al. |
| 2013/0310928 A1 | 11/2013 | Morriss et al. |
| 2013/0325110 A1 | 12/2013 | Khalil et al. |
| 2013/0338763 A1* | 12/2013 | Rowe .................. A61F 2/2427 623/2.11 |
| 2014/0031928 A1* | 1/2014 | Murphy ................ A61F 2/2418 623/2.18 |
| 2014/0039615 A1 | 2/2014 | Padala et al. |
| 2014/0135910 A1 | 5/2014 | Hauser et al. |
| 2014/0200657 A1 | 7/2014 | Maurer et al. |
| 2014/0207230 A1 | 7/2014 | Wilson et al. |
| 2014/0243968 A1 | 8/2014 | Padala |
| 2014/0257347 A1 | 9/2014 | Eidenschink |
| 2014/0276395 A1 | 9/2014 | Wilson et al. |
| 2014/0276971 A1 | 9/2014 | Kovach |
| 2014/0336751 A1 | 11/2014 | Kramer |
| 2014/0350662 A1 | 11/2014 | Vaturi |
| 2014/0379075 A1 | 12/2014 | Maurer et al. |
| 2015/0073547 A1 | 3/2015 | Eliasen et al. |
| 2015/0112429 A1 | 4/2015 | Khairkhahan et al. |
| 2015/0127097 A1 | 5/2015 | Neumann et al. |
| 2015/0134050 A1 | 5/2015 | Solem et al. |
| 2015/0202043 A1 | 7/2015 | Zakai et al. |
| 2015/0223934 A1 | 8/2015 | Vidlund et al. |
| 2015/0257884 A1 | 9/2015 | Subramanian et al. |
| 2015/0305861 A1 | 10/2015 | Annest |
| 2016/0030166 A1 | 2/2016 | Kapadia |
| 2016/0074164 A1 | 3/2016 | Naor |
| 2016/0081798 A1 | 3/2016 | Kocaturk |
| 2016/0089233 A1 | 3/2016 | Lee et al. |
| 2016/0089239 A1 | 3/2016 | Hauser et al. |
| 2016/0113762 A1 | 4/2016 | Clague et al. |
| 2016/0166380 A1 | 6/2016 | Seguin et al. |
| 2016/0166382 A1 | 6/2016 | Nguyen |
| 2016/0184098 A1 | 6/2016 | Vaturi |
| 2016/0193043 A1 | 7/2016 | Kim |
| 2016/0199181 A1 | 7/2016 | Kramer |

(56) References Cited

U.S. PATENT DOCUMENTS

| | | |
|---|---|---|
| 2016/0242909 A1 | 8/2016 | Ketai et al. |
| 2016/0262741 A1 | 9/2016 | Gilmore et al. |
| 2016/0262886 A1 | 9/2016 | Wang |
| 2016/0278920 A1 | 9/2016 | Braido et al. |
| 2016/0287387 A1 | 10/2016 | Wei |
| 2017/0035561 A1 | 2/2017 | Rowe et al. |
| 2017/0196687 A1 | 7/2017 | Braido et al. |
| 2017/0209265 A1 | 7/2017 | Karapetian et al. |
| 2017/0224477 A1 | 8/2017 | Seguin |
| 2017/0239041 A1 | 8/2017 | Quinn |
| 2017/0266003 A1 | 9/2017 | Hammer et al. |
| 2018/0168803 A1 | 6/2018 | Pesce et al. |
| 2019/0209297 A1 | 7/2019 | Metchik et al. |

FOREIGN PATENT DOCUMENTS

| | | |
|---|---|---|
| CA | 2729027 A1 | 12/2009 |
| CA | 2863939 A1 | 8/2012 |
| CA | 2842288 A1 | 1/2013 |
| CA | 2871156 A1 | 11/2013 |
| CA | 2872611 A1 | 11/2013 |
| CN | 102781371 A | 11/2012 |
| CN | 202821715 U | 3/2013 |
| CN | 104768500 B | 10/2017 |
| DE | 102013017750 A1 | 4/2015 |
| DE | 102013017993 A1 | 6/2015 |
| EP | 1796597 A2 | 6/2007 |
| EP | 2032078 A1 | 3/2009 |
| EP | 2150206 A1 | 2/2010 |
| EP | 2849681 A1 | 3/2015 |
| EP | 1871300 B1 | 4/2016 |
| EP | 3023117 A1 | 5/2016 |
| EP | 3042615 A1 | 7/2016 |
| EP | 3056170 A1 | 8/2016 |
| EP | 2023858 B1 | 10/2016 |
| EP | 3081195 A1 | 10/2016 |
| EP | 2032080 B1 | 5/2017 |
| EP | 3187150 A1 | 7/2017 |
| EP | 3241525 A1 | 11/2017 |
| ES | 2586111 T3 | 10/2016 |
| JP | 2013517830 A | 5/2013 |
| JP | 2016512721 A | 5/2016 |
| JP | 2016512726 A | 5/2016 |
| JP | 2016521633 A | 7/2016 |
| RU | 2014153781 A | 7/2016 |
| WO | WO-0060995 A2 | 10/2000 |
| WO | WO-03059209 A2 | 7/2003 |
| WO | WO-2004112658 A1 | 12/2004 |
| WO | WO-2005087140 A1 | 9/2005 |
| WO | WO-2006064490 A1 | 6/2006 |
| WO | WO-2006102329 A1 | 9/2006 |
| WO | WO-2006111391 A1 | 10/2006 |
| WO | WO-2007016097 A2 | 2/2007 |
| WO | WO-2007050256 A2 | 5/2007 |
| WO | WO-2007078772 A1 | 7/2007 |
| WO | WO-2007144865 A1 | 12/2007 |
| WO | WO-2008141322 A1 | 11/2008 |
| WO | WO-2009053952 A2 | 4/2009 |
| WO | WO-2011034973 A3 | 5/2011 |
| WO | WO-2012035279 A1 | 3/2012 |
| WO | WO-2013016618 A2 | 1/2013 |
| WO | WO-2013028387 A2 | 2/2013 |
| WO | WO-2015123597 A1 | 8/2015 |
| WO | WO-2016000274 A1 | 1/2016 |
| WO | WO-2016050751 A1 | 4/2016 |
| WO | WO-2016059533 A1 | 4/2016 |
| WO | WO-2016079734 A1 | 5/2016 |
| WO | WO-2016130706 A1 | 8/2016 |
| WO | WO-2017079234 A1 | 5/2017 |
| WO | WO-2019154927 A1 | 8/2019 |

OTHER PUBLICATIONS

Campelo-Parada, et al., First-in-Man Experience of a Novel Transcatheter Repair System for Treating Severe Tricuspid Regurgitation, *J. Am. Coll. Cardiol.*, 66(22):2475-83 (2015).

Espiritu, et al., Transcatheter Mitral Valve Repair Therapies: Evolution, Status and Challenges, *Annals of Biomedical Engineering*, 45(2):332-359 (2017).

Extended EP Search Report dated Sep. 7, 2018 in EP Patent Application Serial No. 18165070.6.

International Search Report & Written Opinion dated Nov. 17, 2020 in Int'l PCT Patent Appl. Serial No. PCT/IB2020/057368.

International Search Report and Written Opinion dated Jul. 10, 2019 in Int'l PCT Patent Appl. Serial No. PCT/EP2019/053038.

International Search Report dated Dec. 1, 2015 in Intl PCT Patent Appl. No. PCT/EP2015/072388.

Peppas, et al., Preclinical in vivo long-term evaluation of the novel Mitra-Spacer technology: experimental validation in the ovine model, *EuroIntervention*, 13(3):272-279 (2017).

\* cited by examiner

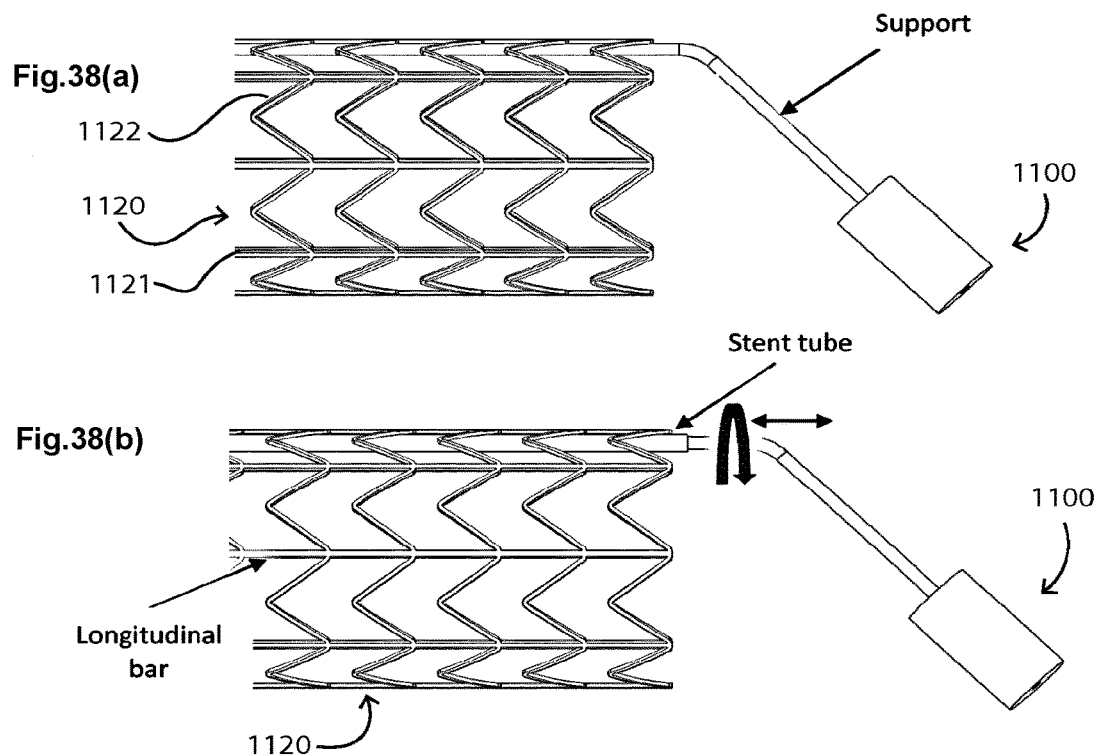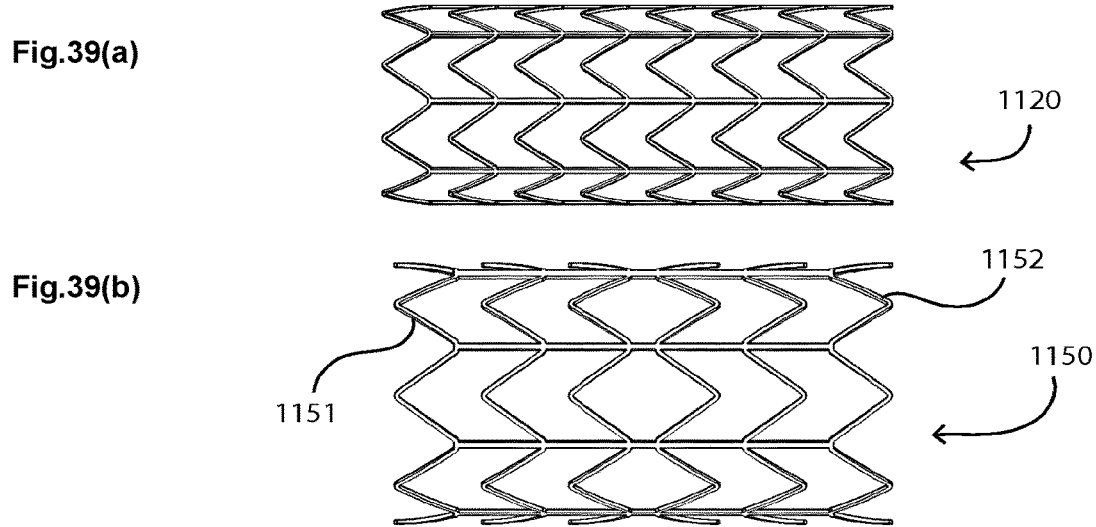

HEART VALVE THERAPEUTIC DEVICE

CROSS-REFERENCE TO RELATED APPLICATIONS

This application is a continuation of U.S. patent application Ser. No. 16/943,621, filed Jul. 30, 2020, now U.S. Pat. No. 10,952,854, which is a continuation of International PCT Patent Application Serial No. PCT/EP2019/053038, filed Feb. 7, 2019, which claims the benefit of priority to EP Patent Application Serial No. 18192480.4, filed Sep. 4, 2018, and EP Patent Application Serial No. 18156125.9, filed Feb. 9, 2018, the entire contents of each of which are incorporated herein by reference.

INTRODUCTION

The invention relates to a heart valve therapeutic device.

It is known, for example from WO2016/050751, to provide a therapeutic device which is deployed to lie across a heart valve.

Other devices are described in US2007/0185571 (Kapadia et al), US2013/0325110 (Khalil et al), and WO2013/028387 (Tendyne Holdings Inc.)

The heart contains four valves, two semilunar, the aortic and pulmonary valves, and two AV valves, the mitral and tricuspid valves. The heart fills with blood from the lungs and body when the AV valves are open. When the heart pumps or contracts, the AV valves close and prevent the blood from regurgitating backwards. The semilunar valves open when the heart pumps allowing the blood to flow into the aorta and main pulmonary artery.

The tricuspid valve is often termed the "forgotten" heart valve, as surgical interventions are carried out on less than 1% (8,000) of the estimated 1.6 m eligible patient population in the US. This is because patients with tricuspid valve disease often have significant co-morbidities and many patients are not candidates for surgery. Even in those who are fit for surgery the risks are high with an operative mortality of between 10% and 35%. Thus, there is a significant clinical need for a minimally invasive solution.

It has been demonstrated in a research publication that the implantation of AV balloon spacers in the mitral position is safe and feasible in ovine models [EuroIntervention, 2017 Jun. 20; 13(3):272-279], https://www.ncbi.nlm.nih.gov/pubmed/28262622

Furthermore this type of procedure has been proven safe and additionally effective in patients when a similar device has been implanted in the tricuspid position [J Am Coll Cardiol 2015; 66:2475-83]. This clinical study demonstrated that improvements in patient's NYHA functional status could be achieved and pronounced reductions in the presence and severity of peripheral edema could also be achieved. However, the two devices used these studies have a limiting factor: they do not allow blood to flow through the centre of the device, thus the overall diameter of balloon (or solid) spacers is limited, as the remaining area for blood to flow around the device becomes prohibitively small as the devices become larger. Another limiting factor with these devices is that the surface that the native mitral or tricuspid leaflets impact on is relatively "hard" and this may have detrimental effects on the leaflets in the patient's heart.

While the invention disclosed in this document is intended to be used in adult human patients, it could also be used in paediatric patients. It could also be used for the treatment of animals; for example, dogs and horses.

The present invention is directed towards providing a device and method of deployment and use which:
(a) is simple to deploy accurately for reliable operation, and/or
(b) is effective for reliable operation in performing the valving function with minimum regurgitation or undesired blood flows of any type.

In this specification, the term "proximal" means the direction closest to entry of the device into a patient's blood vessel, and "distal" further from this position.

SUMMARY OF THE INVENTION

Described herein is a heart valve therapeutic device comprising:
  a support,
  a coaptation assist valve comprising:
    a conduit comprising a side wall and being mounted to the support to reside across a heart valve, in use,
    the conduit having a radial dimension, and having an axial dimension between a proximal end and a distal end,
    the conduit being configured to allow blood flow through a channel within the conduit,
    said side wall has an external surface for coaption with native leaflets, and a valve mounted within the conduit.

We describe therapeutic devices as set out in various embodiments in the appended claims 2 to 119.

Also, we also describe other therapeutic devices, especially for heart valve treatment, which do not necessarily have a prosthetic valve and/or a conduit, but have the benefits of the support of various embodiments.

The device may for example be a heart mitral or tricuspid valve therapeutic device comprising a support, and a coaptation assist valve comprising a conduit mounted to the support and having a radial dimension and an axial dimension to reside across a heart valve, being configured to allow blood flow through a channel within the conduit, and having an external surface for coapting with native leaflets. There is preferably a valve mounted within the conduit.

The conduit may include flexible material providing a native leaflet contact surface which is yielding in at least some parts.

Preferably, the conduit is of flexible material, such as for example pericardium, to expand to provide a compliant surface for coapting with native leaflets. The conduit may be made from rigid or semi rigid material. The coaptation assist valve may have a distal structure to support the distal end of the coaptation assist valve. Preferably, the coaptation assist valve has a proximal structure to support the proximal end of the coaptation assist valve.

The coaptation assist valve may have distal and proximal structures arranged to support the distal and proximal ends of the coaptation assist valve. Preferably, the distal structure comprises a ring, and the proximal structure may comprise a ring.

The coaptation assist valve may be connected to the support at or near its distal end. Preferably, the coaptation assist valve is connected to the support at or near its proximal end.

The coaptation assist valve may be connected to the support at or near both its distal and proximal ends. The distal structure may have spokes for connecting to the support. The proximal structure may have spokes for connecting to the support. The coaptation assist valve may be connected to the support by tethers. The distal structure may be connected to the support by tethers. The proximal structure may be connected to the support by tethers. The distal and proximal structures may be connected to the support by tethers. The tethers may comprise cables.

Preferably, the conduit has a length in the range of 10 mm to 45 mm. Preferably, the conduit has a radial dimension in the range of 5 mm to 45 mm. Preferably, the conduit has a generally tubular shape, and it may have a larger radial dimension at its proximal end than at its distal end, for example a truncated cone shape. The conduit may have a substantially circular cross section along at least part of its length.

Preferably, the conduit material is sufficiently flexible to form a convex shape during systole, in use. The conduit may have less structural support between the distal and proximal ends than at said ends. The conduit may have a cross sectional area decreasing in the distal direction.

Preferably, the coaptation assist valve is free to position/orientate itself within the native valve, preferably by way of flexible support elements such as tethers. Preferably, the support extends through the coaptation assist valve.

The support may comprise an elongate rail and at least one connector connecting the coaptation assist valve to the rail.

The support may have a pre-set bend. The support may be steerable and/or lockable. The support may include a guide. Preferably, the guide has a preset bend to guide position and/or orientation of the support. Preferably, the guide is steerable and/or lockable.

The support may have variable properties along its length. The guide may have variable properties along its length.

Preferably, the support extends only distally of the distal end of the coaptation assist valve. Preferably, the rail extends only proximally of the proximal end of the coaptation assist valve. Preferably, the support comprises an anchor for fixing to tissue such as a ventricle wall. The anchor may comprise a corkscrew element.

Preferably, the support comprises a rail or steerable guide of variable strength or stiffness along at least some of its length. Preferably, the connector extends at least partially radially to link the rail with the coaptation assist valve. Preferably, at least one connector is flexible, allowing radial movement of the coaptation assist valve with respect to the rail.

The connector may comprise tethers. Preferably, at least one connector is rigid, preventing radial movement of the coaptation assist valve with respect to the rail.

Preferably, the valve is arranged to allow diastolic blood flow and to prevent systolic blood flow. Preferably, the valve comprises one or more prosthetic leaflets mounted within the conduit. The valve may comprise prosthetic valve elements shaped like native leaflets. Preferably, the valve leaflets are cup shaped. Preferably, the valve is positioned near the proximal end of the coaptation assist valve. Preferably, the valve leaflets are each or all created from one sheet of material. The valve may be made from the same material as the conduit.

The valve leaflets may contain at least one fenestration. The valve may comprise two leaflets or three leaflets, for example.

Preferably, the valve is secured to a coaptation assist valve proximal support structure, which preferably comprises a ring.

The device may further comprise a biasing element arranged to bias at least part of the support towards a vessel wall, limiting lateral movement. The biasing element may be arranged to bias the guide towards a vessel wall, limiting lateral movement. The biasing element may comprise shaped wire and/or a stent or stent-like structure. The biasing element may be arranged to limit lateral, axial and/or rotational movement.

The support may be arranged to be fixed to a patient's body near an operator. The guide may be arranged to be fixed to a patient's body near an operator.

Preferably, the support comprises and elongate support and/or a guide, and said elongate support and/or guide are arranged to be fixed to a patient's body by two-part fixation a first part mechanically fixed to the body in advance of positioning the support and/or guide, and a second part activated after positioning the support and/or guide.

The device may include an additional support configured to extend into another vessel to enhance stability.

In another aspect we describe a guide arranged to vary curvature of an elongate support in a medical device, especially a medical device for internal use, such as extending through a blood vessel. The guide may have a preset bend to guide position and/or orientation of the support. The guide may be steerable and/or lockable, such as by straightening an elongate member with a pre-formed bend. The guide may have telescopic tubing, which may for example be around a still rod, which may extend into a rigid tube.

The support may include an element that can be advanced relative to a bend in the guide to position the support relative to the bend, and the element may comprise rigid telescopic elements to enhance stability on the guide. The support may have variable properties along its length and/or the guide may have variable properties along its length.

In a further aspect we describe a biasing element for biasing an elongate support or other elongate member of a medical device to a position in vessel, the biasing element being arranged to bias at least part of the support towards a vessel wall, or to a desired location within a vessel, limiting lateral movement. The biasing element may be arranged to bias the guide towards a vessel wall, limiting lateral movement. The biasing element may comprise shaped wire. The biasing element may comprise a stent or a stent-like structure, and such a structure may optionally include a tube to receive the support or other member being biased. Also, the biasing element may be arranged to limit lateral, axial and/or rotational movement, and may retain the support in a central, axial, position or another position between axial and an outer position at the circumference of the stent-like apparatus.

In other aspects we describe methods of use of apparatus of any embodiment. Examples are for delivery to a patient heart mitral or tricuspid valve and deploying at this site so that the patient's native leaflets can contact the conduit.

In another aspect the device is adapted to primarily act as a flexible conduit. In this case the device may be for treating regurgitation of a native heart valve, the device comprising in one example: a conduit configured to reside across a native heart valve, the conduit having a lumen and a flexible sidewall for coapting with leaflets of the native heart valve, a prosthetic valve mounted within the lumen; and a support rail configured to suspend the conduit across the native heart valve.

In other aspects the device is for treating regurgitation of a native heart valve, and comprises: a conduit having a lumen, a sidewall, a distal end and a proximal end, the conduit configured to reside across a native heart valve so that the sidewall coapts with leaflets of the native heart valve; a structural support disposed at each of the distal end and the proximal end; a prosthetic valve mounted within the lumen; and a support rail coupled to the structural supports and disposed at each of the distal end and the proximal end.

Also, the device may take any form for use in a blood vessel and which has a lockable rail with one or more features set out below. For example, the device may be for treating regurgitation of a native heart valve, the device comprising: a conduit configured to reside across a native heart valve, the conduit having a lumen and a sidewall for coapting with leaflets of the native heart valve, and a prosthetic valve mounted within the lumen; a guide having proximal and distal ends; and a support rail operatively associated with the guide, the support rail having a proximal portion and a distal portion, the distal portion coupled to the conduit to suspend the conduit across the native heart valve.

In various embodiments we describe a device which has a conduit which is suspended. The device may be for treating regurgitation of a native heart valve, the device comprising: a conduit configured to reside across a native heart valve, the conduit having a lumen and a sidewall for coaption with leaflets of the native heart valve, and a prosthetic valve mounted within the lumen; and a support rail configured to suspend the conduit across the native heart valve without anchoring of the support rail to an annulus of the native heart valve or atrial or ventricular tissue adjacent to the native heart valve.

DETAILED DESCRIPTION OF THE INVENTION

Brief Description of the Drawings

The invention will be more clearly understood from the following description of some embodiments thereof, given by way of example only with reference to the accompanying drawings in which:—

FIGS. 9(a) and 9(b) are side views showing an expandable hollow conduit before and after expanding respectively shows an embodiment where the hollow conduit is inflatable, in which FIG. 9(a) shows the conduit in its normal configuration and FIG. 9(b) shows it after inflation with saline or another material, and in which the structure of the inner wall of the inflatable conduit prevents deformation;

FIG. 38(a) shows a biasing element in the form of a stent for retaining a support rail against a blood vessel; and FIG. 38(b) shows a biasing element which is stent-like and attached to a tube, allowing axial and rotational movement of the coaptation member relative to the stent;

FIG. 39(a) shows a stent which has hoops with zig-zag patterns facing in one direction, and FIG. 39(b) shows a stent which has hoops with zig-zag patterns facing in two directions.

DESCRIPTION OF THE EMBODIMENTS

Heart valve therapeutic devices may comprise a conduit with an outer surface for coaption with the native leaflets, a prosthetic valve within the conduit to allow one-way flow, and a support for positioning the conduit across the native leaflets.

Figure 1:
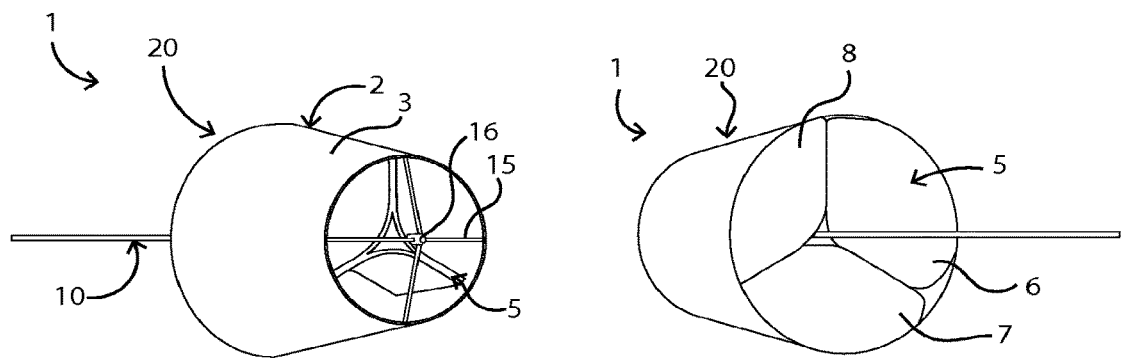
FIG. 1 is a pair of perspective views of a heart valve therapeutic device of the invention, form the distal (left) and proximal (right) ends (conduit with valve, support, and fixation between the spacer and the support)

Referring to FIG. 1, a heart valve therapeutic device 1 comprises a coaptation assist valve 20 comprising:

a hollow conduit 2 with an outer surface 3 for coaption with the native leaflets, and defining an internal lumen or channel for blood flow, a prosthetic flow valve 5 with three prosthetic leaflets 6, 7, and 8 mounted within the conduit 2 to allow substantially only one-way flow through the conduit 2.

Support for the coaptation assist valve 20 is provided by an elongate support 10 for positioning the conduit 2 across the native leaflets, and connectors 15 attaching the conduit 2 to the support 10. The hollow conduit 2 has in preferred embodiments its proximal end in the atrium, in use, and the distal end in the ventricle.

The valve 5 prosthetic leaflets are configured to form cup-shaped barriers to flow when flow is systolic. The three valve leaflets 6-8 co-operate to prevent flow during the systolic period when the device is inserted across the tricuspid or mitral heart valves. The valve leaflets are made from pericardium tissue and are sutured to the conduit or the frame, either directly or through other parts.

Figure 2:
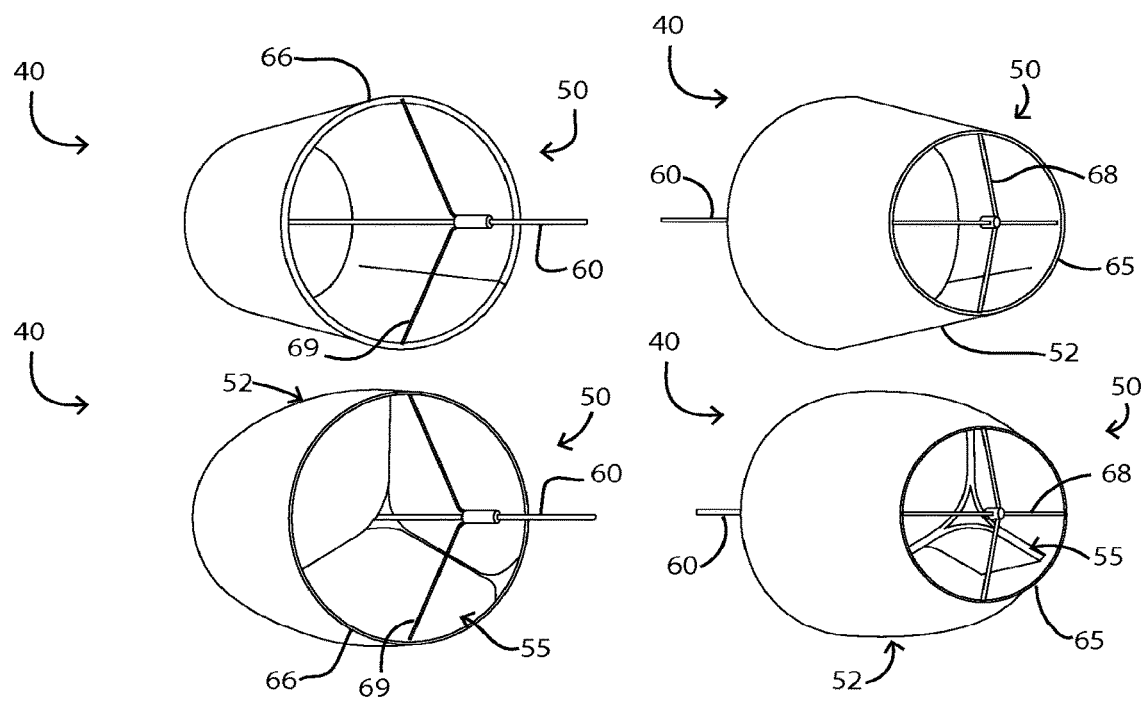
FIG. 2 is a set of two pairs of perspective views, in the left side from the proximal end diastole and systole, and on the right from the distal end, again both diastole and systole.

Another preferred device, 40, is shown in FIG. 2. This comprises a coaptation assist valve 50 comprising:

a compliant conduit 52 for coapting with the native leaflets;

a prosthetic valve 55 within the conduit 52 for one way flow through the conduit 52, again comprising three prosthetic leaflets within the conduit 52;

a distal ring 65 to add structural support to the distal end of the conduit 52; and a proximal ring 66 to provide structural support to the proximal end of the conduit 52.

Support for the coaptation assist valve 50 is provided by:

an elongate support 60 for positioning the conduit 52 across the native leaflets, distal connectors or tethers 68 attaching the distal ring 65 to the elongate support 60, and proximal connectors or tethers 69 attaching the proximal ring 66 to the elongate support 60.

For clarity the elongate support of various embodiments is also referred to as a support rail. The support may for example comprise a rail and tethers extending from the rail to each end of the conduit. Also, in the terminology used here, a "coaptation assist valve" is a combination of a conduit and a prosthetic valve within the channel of the conduit.

In various embodiments, the conduit and/or the prosthetic valve is made from compliant material, such as bovine or porcine pericardium, or pericardium from another species. The conduit and/or prosthetic valve may also be made from other materials, such as composites, polymers, metals, solid and partially filled structures such as braids and coils, or any other types and configurations of materials. The conduit may be configured to expand during systole as pressure builds within the conduit, and to relax during diastole as blood flows through the conduit. This expansion and relaxation can help with washing blood from the conduit, reducing the risk of blood stasis and clotting. The conduit coapting (external radial) surface acts as a "soft" element that the native leaflets can coapt against in an atraumatic manner, with similar pressures so that the coaptation surface deforms to fill the regurgitant orifice area. When pressurised during systole, the conduit may become convex in shape (bottom diagrams of FIG. 2), and can have a larger diameter centrally than the proximal and distal ends. During diastole, the compliant conduit relaxes as blood flows within and/or around it.

In various embodiments, the orientation or position of the coaptation assist valve is flexible to respond to cardiac motion and to ensure optimal positioning within the regurgitant orifice area of the native valve, with the coapting surface tilting with respect to the support.

The conduit shape shown in FIGS. 1 and 2 is a truncated cone, with a smaller diameter at the distal end. The conduit in FIG. 2 has a proximal diameter of 20 mm and a distal diameter of 15 mm. The conduit preferably has a diameter of between 5 mm and 55 mm at the distal end and between 5 mm and 55 mm at the proximal end. The conduit also has a length to ensure coaptation with the native valves. The length in the embodiment in FIG. 2 is 20 mm, and this length is preferably between 5 mm and 45 mm. The truncated cone shape of the conduit may allow for the selective reduction of regurgitation. Advancing the conduit distally can increase the coaption area of the conduit, and retracting the conduit proximally can reduce the coaption area of the conduit. A non-tapered cylindrical shape may also be effective.

The prosthetic valve within the conduit allows substantially only one-way flow through the conduit, preventing flow during systole, and allowing flow during diastole. In a preferred embodiment, the valve element has three leaflets as shown, but can have any suitable number of at least one leaflet. The valve 5 in FIG. 1 is connected to the inner surface of the conduit. The leaflets may be attached to a structural frame and/or the conduit at any point along their length. The leaflets of the prosthetic valve may be shaped like native leaflets and/or cup-shaped. Preferably, the valve is secured to a conduit proximal support structure, which may comprises a ring, but is may also be connected directly to the conduit sidewall.

Figure 3:
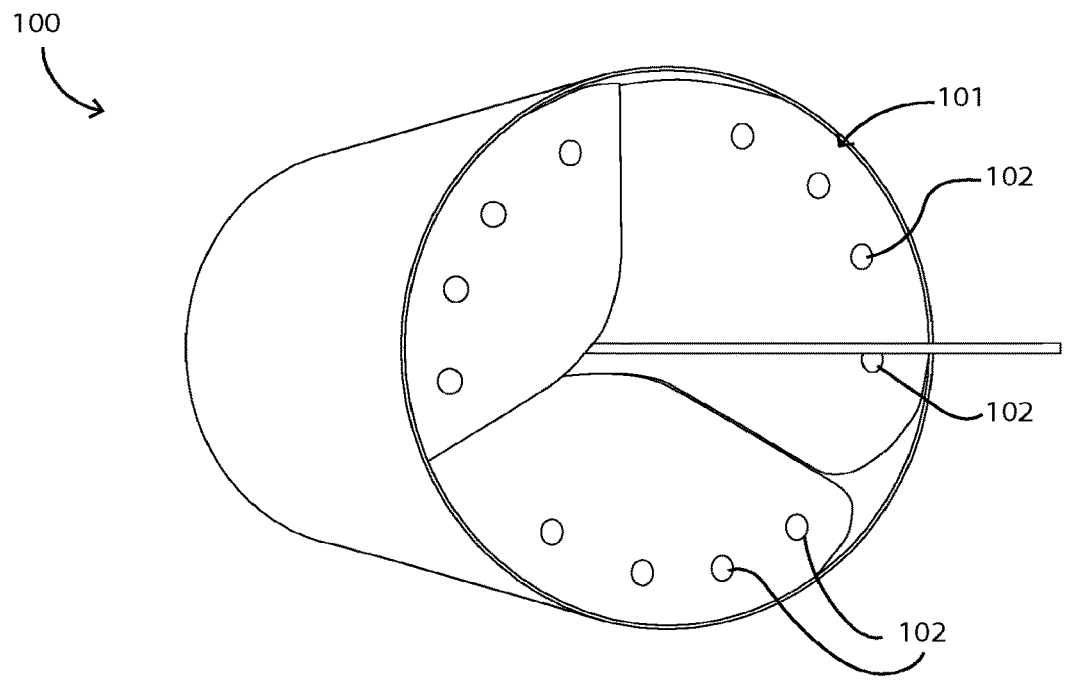
FIG. 3 is a perspective view from the proximal end of an alternative device, incorporating fenestrations in valve elements.

The leaflets may include fenestrations to support washing jets to prevent or reduce thrombosis and/or stasis. FIG. 3 shows a coaption assist valve 100 having a valve with three prosthetic leaflets 101 with fenestrations 102. In this case the fenestrations 102 are arranged in a ring, four per prosthetic leaflet. However, there can be at least one fenestration in the device, and may be any shape, such as circular, oval, square rectangular, or any combination of these shapes.

Figure 4:
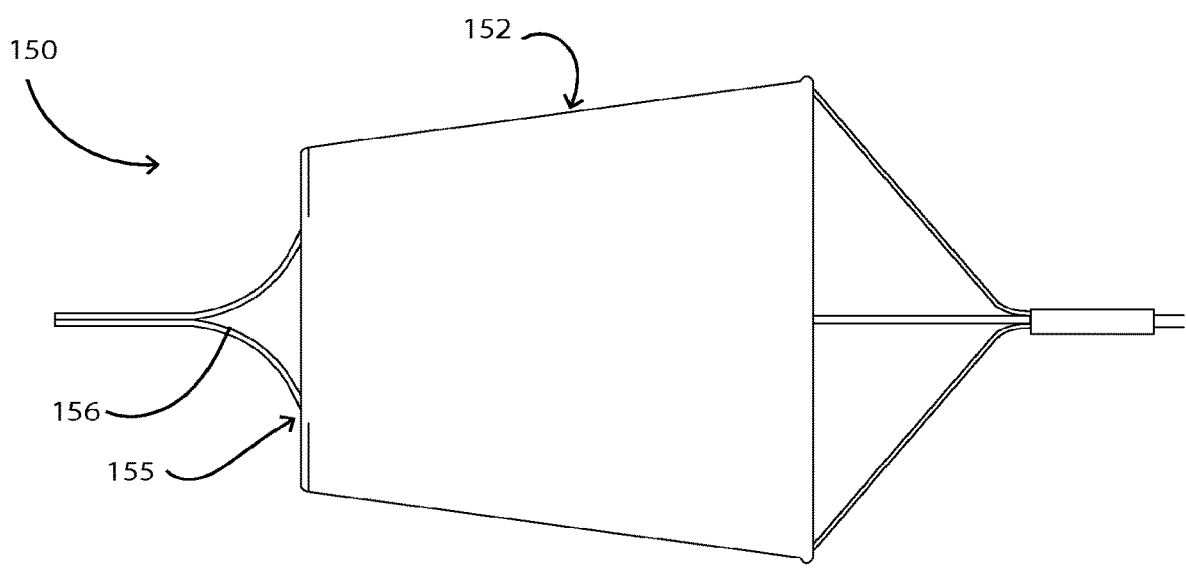
FIG. 4 is a side view of a device, in which a valve element extends outside of the conduit of the device.

In a preferred embodiment, the proximal end of the valve is positioned near the proximal end of the conduit. However, the valve may alternatively be located near the distal end or between the distal and proximal ends. The valve may also partially extend distally of the conduit. Referring to FIG. 4, the valve may be towards the distal end of a conduit 152, with a distal end 156 of a valve 155 extending distally from the conduit 152, in a device 150.

Figure 5:
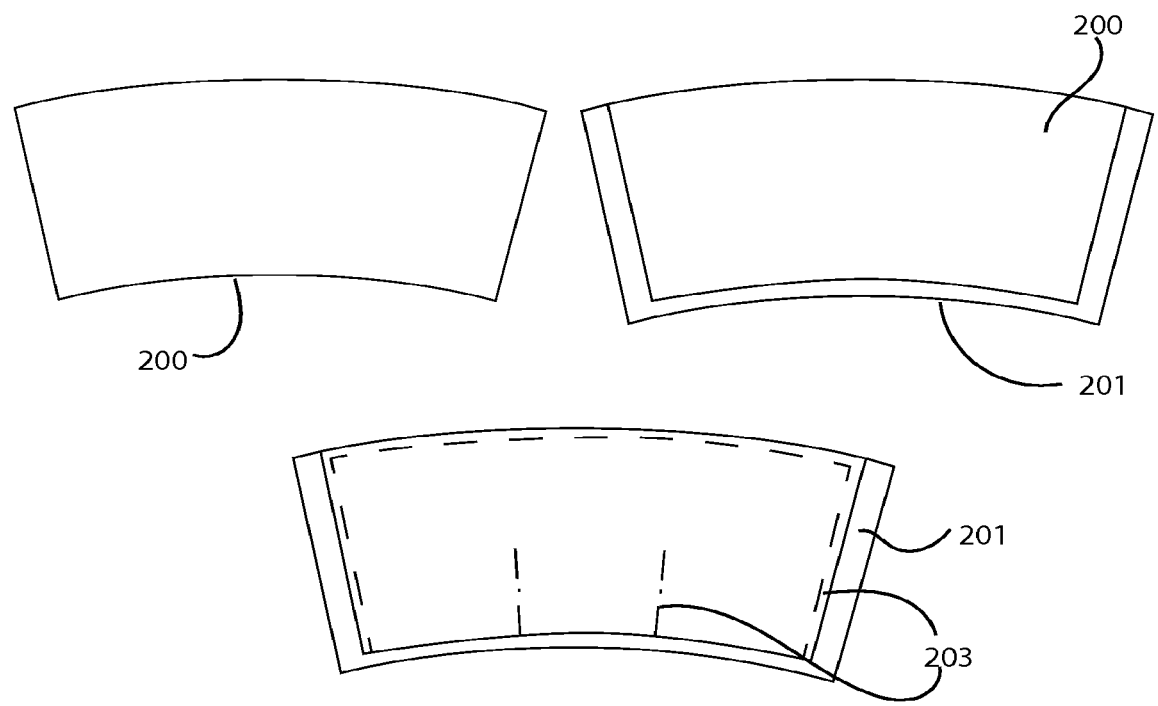
FIG. 5 is a top view of material cut to a flat pattern for the valve (left) and a top view of this material placed on a cut pattern for a conduit, and a view showing suture lines.

The leaflets can be created from one sheet of material and creating fixation points to the inner surface of the conduit. FIG. 5 shows a valve sheet 200, a conduit sheet 201, and sutures 203. However, each individual leaflet may be created separately and fixed to the conduit and/or frame at defined points. Typically, the valve element(s) is made from the same material as the conduit side wall but may also be made from a different material than the conduit.

The coaptation assist valve preferably has a distal ring or other structure, such as a frame, to ensure that the distal end of the conduit remains open. With the open distal end, systolic flow can pressurise the conduit to expand outwards to enhance coaptation with the native valves, while activating the valve within the conduit to prevent systolic flow through the conduit.

Preferably, the distal structure is part of a frame which may be made from laser-cut Nitinol tube or sheet material but may alternatively use other manufacturing methods such as wire forming. However, the distal structure may be included with or replaced by other forms of distal structure such as laser cut, braided, wire formed metal or polymer shapes.

The coaptation assist valve also preferably comprises a proximal support structure, such as a frame, to ensure that the proximal end of the conduit remains open. With the open proximal end, diastolic flow is encouraged through the conduit, opening the valve to approach the inner surface of the conduit, removing stagnant blood within the conduit, reducing stasis and clotting. The proximal structure preferably is part of a frame, which is preferably made from a laser cut Nitinol tube or sheet material, but may alternatively use other manufacturing methods such as wire forming. However, the proximal structure may be included with or replaced by other forms of structure such as laser cut, braided, wire formed metal or polymer shapes. Both these structures may be located at or near the extremities of the conduit, keeping stiff elements away from the region of coaption with the native leaflets. Both distal and proximal structures may include connection parts such as holes or other structures to facilitate connection to tethers and/or the conduit which connect them to the support.

Figure 6:
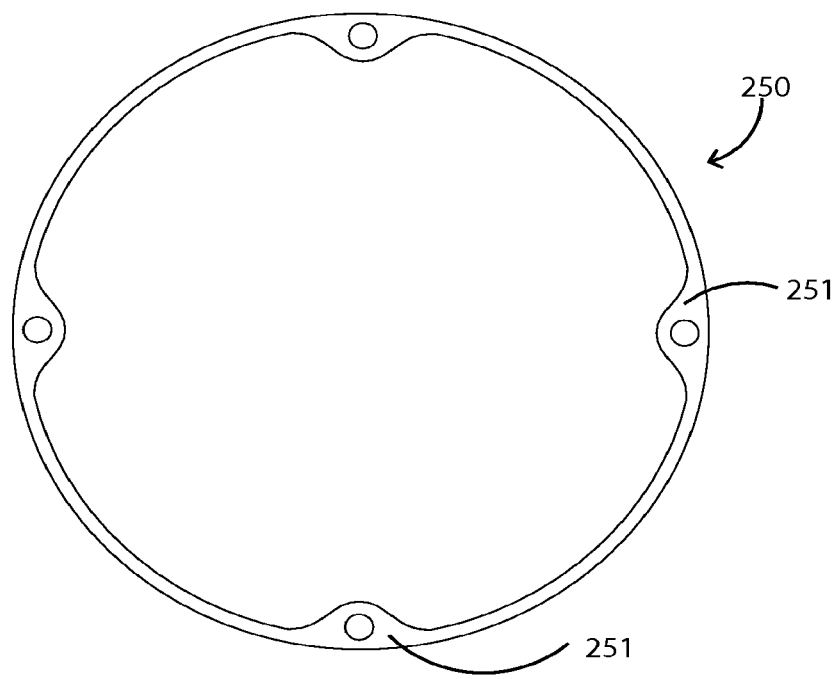
FIG. 6 is an end view of a laser-cut ring with eyelets for connection to tethers.

FIG. 6 shows a ring 250 having eyelets 251 at 90° circumferential spacings, and support tethers can be attached through the eyelets. While four equi-spaced eyelets are shown here, in other embodiments there may be a different number. In many cases it is preferred that there are three tethers, especially if there are three prosthetic valve leaflets. In general it is preferred that there by the same number of tethers as leaflets.

Figure 7:
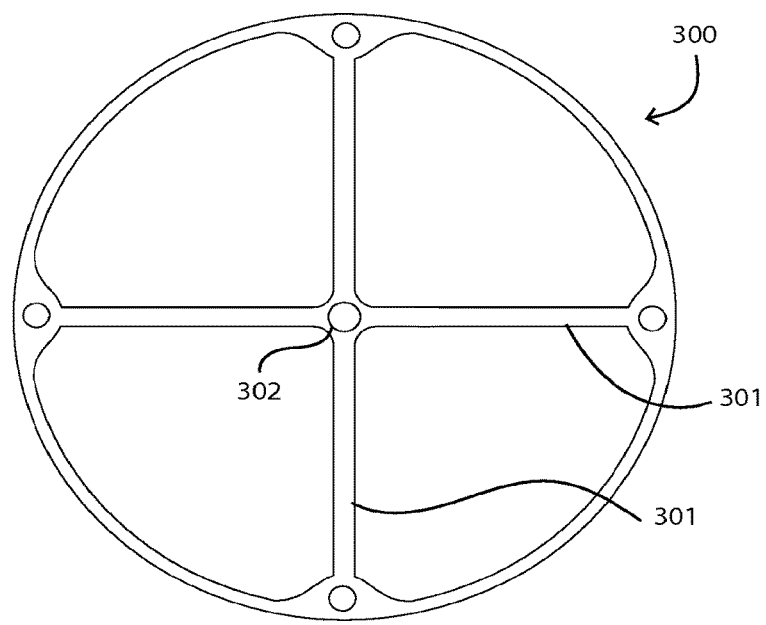
FIG. 7 is an end view of an alternative laser-cut ring, in this case with spokes for connection to an axial support.

The distal and/or proximal ring structure may include a connection part for connection to a support: an example being a structure 300 with a ring and spokes 301 as shown in FIG. 7. The spokes 301 extend from a central hub having a through-hole 302 for receiving the support. The distal and proximal structures may be made as one part, in a dumbbell like structure. This can include spokes as shown in FIG. 7. Spokes can be straight, curved or irregularly shaped.

Figure 8:
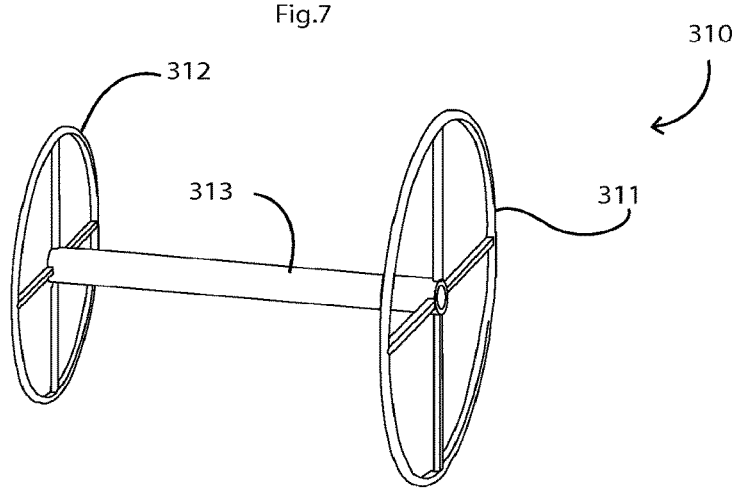
FIG. 8 shows the distal and proximal structures being formed from one part, each comprising a ring with spokes, and a tube connecting them.

FIG. 8 shows the distal and proximal structures being formed from one part, 310. There is a proximal ring 311 and a distal ring 312 each having spokes, and a tube 313 connecting them.

Figures 9A, 9B:
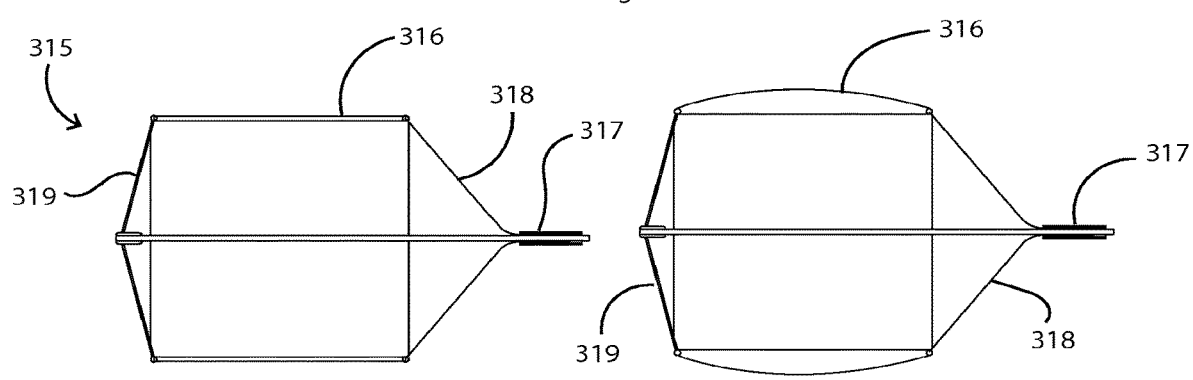

In another embodiment the conduit is a hollow and expandable structure. For example, the inner diameter remains constant, but the outer diameter is expanded by injection of saline or another fluid. The substance may be compliant (such as an injectable polymer) or rigid (such as a cement-like material) and may also be removable. In such an embodiment, the coaptation diameter can be selected and adjusted, while the valve diameter preferable remains constant. Referring to FIGS. 9(*a*) and 9(*b*) the conduit has an expandable wall 316 with two leaves and supported by a support rail 317 and proximal tethers 318 and distal tethers 319. The wall 316 outer leaf expands from a substantially cylindrical shape to a barrel shape (FIG. 9(*b*)) with a generally convex outer surface. The conduit may be expandable after delivery. The conduit may be expandable by a mechanism including injection of saline or other fluids or solids in the annular space between the two leaves of the conduit wall. This can have the benefit of selecting and/or adjusting the effective coaptation area. Injection of a "soft" material or fluid may also reduce trauma associated with contact of the native leaflets with the coaptation surface.

Devices of various embodiments comprise distal tethers which connect the distal end of the conduit to the support. In the embodiment in FIG. 2, the distal tethers 68 limit axial motion of the conduit 52 relative to the elongate support 60. The distal tethers may be rigid or flexible, and if flexible, the extent of flexibility can be set by choice of material to provide the desired level of allowed movement of the coaptation assist valve relative to the support rail.

Figure 9C:
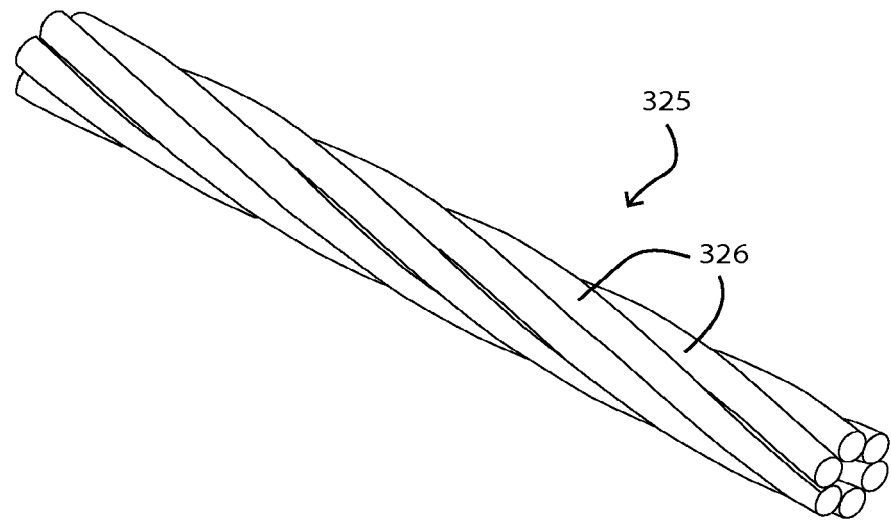
FIG. 9(c) shows strand cables used as tethers due to their flexibility in compression and high strength in tension.

In one embodiment, the distal tethers are made from metal strand cables. Referring to FIG. 9(c) a tether 325 has inter-twined strands 326. Such a tether has a high strength in tension to prevent axial movement of the conduit during systole, and the flexibility to relax during diastole. In the preferred embodiment, the distal and proximal tethers are part of the frame which supports the valve and conduit. The distal and/or proximal structures can be connected to the support by welding, bonding, suturing, crimping or any other method known by one skilled in the art.

Flexible tethers may also allow the centre of the coaptation assist valve to move eccentrically relative to the centre of the support; this enables "self-positioning" of the coaptation assist valve within the regurgitant orifice, as the native leaflets push the coaptation assist valve towards the regurgitant orifice. The distal tethers in FIG. 2 are approximately 0.4 mm in diameter, and in general preferably have a diameter of 0.1 mm to 4 mm, or equivalent area if not circular. However, the distal tethers may be solid and further limit movement of the coaptation assist valve relative to the support during systole and diastole. The distal tethers may be connected to the support, distally, proximally or in line with the distal end of the conduit. The distal tethers may comprise round wire, tube, cable or hollow cable. However, the distal tethers may alternatively comprise flat wire, spring elements or elements of any other suitable shape. The distal tethers may comprise materials such as polymers or metals (including sutures) or other materials. Distal and proximal tethers may be laser cut, possibly from the same piece as the distal and/or proximal structures.

Devices of various embodiments have supports comprising proximal tethers for the coaptation assist valve. The proximal tethers connect the proximal end of the coaptation assist valve to the support rail. In the embodiment in FIG. 2, the proximal tethers 69 limit motion of the coaptation assist valve relative to the support rail 60. The proximal tethers may be rigid or flexible. In one embodiment, the proximal tethers are part of the conduit frame. An alternative is that they are made from metal strand cables, due to their high strength in tension to prevent axial movement of the coaptation assist valve during diastole, and the flexibility to relax during systole. Tethers may be flexible enough to allow the centre of the coaptation assist valve to move eccentrically relative to the centre of the support; this enables "self-positioning" of the coaptation assist valve within the regurgitant orifice, as the native leaflets push the coaptation assist valve towards the regurgitant orifice. The proximal tethers shown in FIG. 2 are approximately 0.4 mm in diameter, and typically have a diameter of 0.05 mm to 4 mm in diameter, or equivalent area if not circular. However, the proximal tethers may also be solid and prevent movement of the coaptation assist valve relative to the support during systole and diastole. The proximal tethers may be connected to the support, distally, proximally or in line with the proximal end of the conduit. The proximal tethers are typically made from round wire, tube, cable or hollow cable. However, the proximal tethers may also be made from flat wire, spring elements or any other shape. The proximal tethers may also be made from other materials such as polymers or metals (including sutures) or other materials.

The conduit of various embodiments may be made selectively less compliant by activation of the distal and proximal tethers. Where there is a lot of slack in the distal and proximal tethers, the conduit can move eccentrically and axially relative to the support, and support significant bulging of the conduit during systole. Where the tension in the distal and proximal tethers is maximised, the conduit position is fixed relative to the support, and the conduit experiences less bulging during systole. In preferred embodiments, tension is applied to tethers to allow limited movement of the conduit relative to the support, allowing the coaptation assist valve to "self-centre" towards the centre of the regurgitant orifice and for limited bulging of the conduit to increase coaption with the native leaflets. Proximal and/or distal tethers may also be slidable along the support and biased into tension by spring elements.

In various embodiments the coaptation assist valve is fixed to a support which is used to position the coaptation assist valve within a native valve. In preferred embodiments, the support extends from outside a peripheral vessel (such as the jugular or subclavian vein), percutaneously delivered through the SVC, the right atrium and into the ventricle, as shown for a coaptation assist valve 330 in FIG. 10. In this embodiment, the support is a rail, and is guided into position using a steerable guide. The rail extends through the centre of the coaptation assist valve and is attached to the distal and proximal ends of the coaptation assist valve with tethers. The inherent stiffness of the support prevents migration of the coaptation assist valve proximally during systole, and distally during diastole. The support may have suitable stiffness to permit limited bending of the support to enable the conduit to be self-centered.

Figure 10:
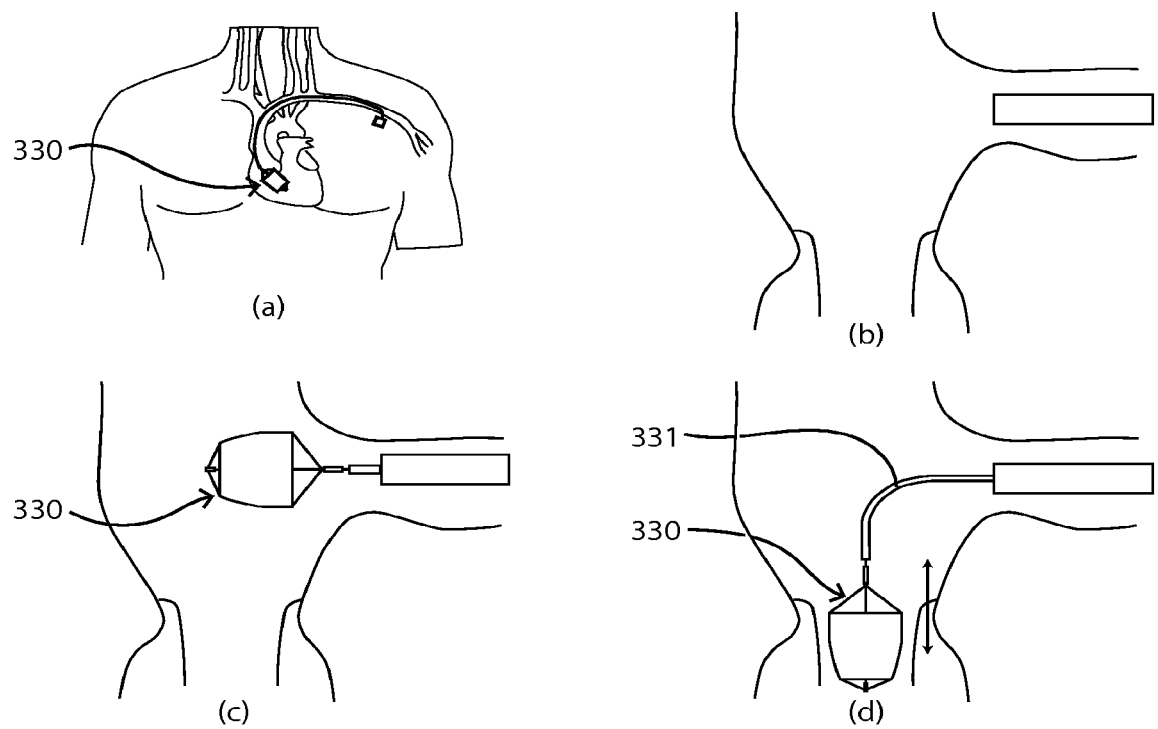
FIG. 10 is a diagram showing a coaptation assist valve passing through the SVC and fixed outside the subclavian vein.

FIG. 10 shows:
(a) Delivery route of the valve 330 through the subclavian vein, through the SVC and into the right atrium; there are many alternative delivery routes, two of which are through the left and right jugular veins.
(b) Coaptation assist valve 330 (shown diagrammatically as a rectangular outline in side view) is delivered collapsed in a sheath to the right atrium.
(c) Coaptation assist valve 330 is advanced into the right atrium and expands when leaving the sheath.
(d) A steerable collar 331 is used to point the coaptation assist valve 330 into the centre of the native valve; the coaptation assist valve 330 can be advanced and retracted relative to the steerable collar 331 to optimise the axial position.

Figure 11:
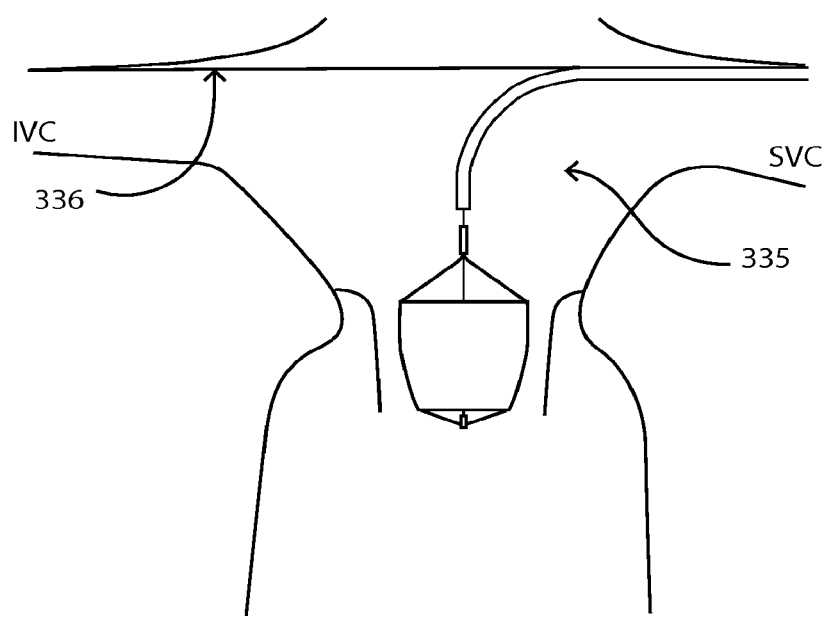
FIG. 11 shows a device additionally supported by a rail that passes from the SVC into the IVC.

In a preferred embodiment, the support comprises an elongate member, referred to as a support rail. The rail may have varying stiffness along its length. The rail may be suitably flexible to allow movement of the coaptation assist valve with cardiac and respiratory movement. The rail may have varying properties along its length. For example, the rail may be flexible at its distal end to allow movement for self-centering while being stiffer more proximally to prevent axial movement of the support. In another embodiment, the heart valve therapeutic device may be delivered from the groin, through the IVC and to the right atrium. The device may also be delivered to and used to prevent regurgitation in other valves in the heart. In a further embodiment, as shown in FIG. 11 a device 335 may be delivered from the SVC with an additional support 336 extending into the IVC for stability. This additional support may be fixed or biased in the IVC, but preferably will be "wedged"/biased into position by the curvature of the IVC. The steerable guide can be used to orientate the coaptation assist valve towards the native valve on a different axis to the additional support. Similarly, this additional support can be positioned in the SVC after delivery through the IVC, or between any two vessels proximate to the delivery path.

Figure 12:
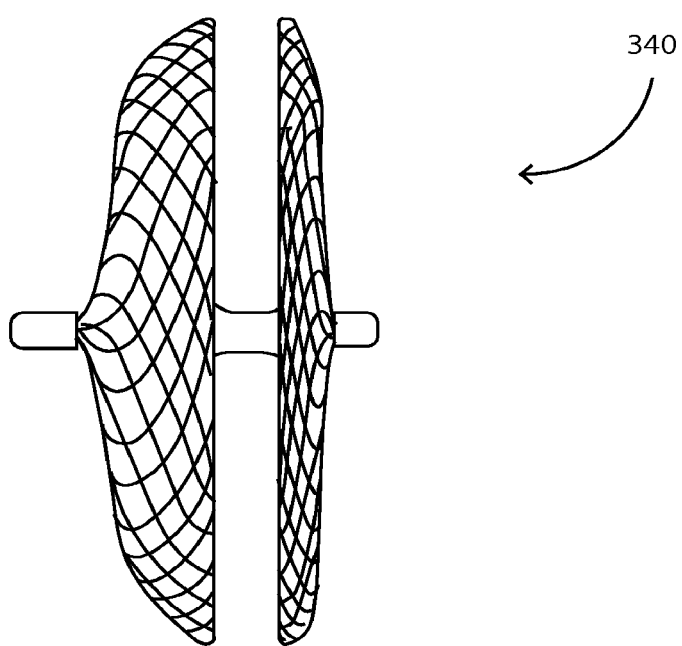
FIG. 12 shows an amplatzer device, which can be used to stabilise the coaptation assist valve across the septum.

The device can also be used for the repair of regurgitation of the mitral valve. The device can be delivered through the IVC or SVC, across the septum and positioned within the regurgitant orifice of the mitral valve. Further stability can be achieved by having an amplatzer type stabilisation element at either side of the septal wall (FIG. 12), which the rail would operatively associated with In the preferred embodiment, the rail passes through the stabilisation element. FIG. 12 shows an amplatzer-like device 340, which can be used to stabilise the anchor and support across the septum (Berger et al, *The Journal of Thoracic and Cardiovascular Surgery*, Volume 118, Issue 4, October 1999. Pages 674-680). In this configuration, the rail passes from the right atrium, through the septal wall and suspends the conduit across mitral valve.

Figure 13:
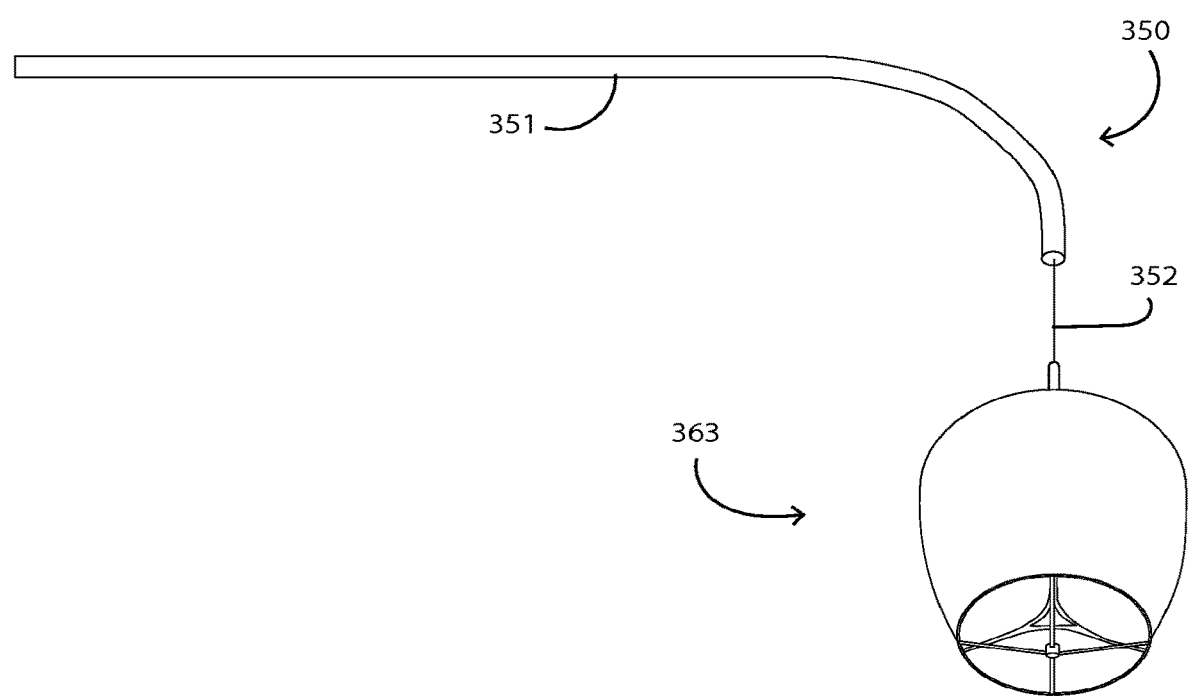
FIG. 13 is a perspective view showing a heart valve therapeutic device with a stiff collar for providing a desired shape.

The support rail can in various embodiments be steered and locked in position using a guide. In the preferred embodiment, the guide consists of a steerable stylet or collar; the support rail can then be advanced or retracted relative to the stylet/collar to improve the axial position of the support rail and of the coaptation assist valve that it is supporting (FIG. 13). FIG. 13 shows a device 350 having a guide collar 351 surrounding a support rail 352, supporting the assembly 353 of the coaptation assist valve and associated components. The use of a steerable support rail gives control over both the steering angle and the axial position of the coaptation assist valve.

Regarding terminology, the word "support" means all of the components which are used in supporting the coaptation assist valve. This may include a rail and tethers extending radially to the assist valve, and it may include as noted above a guide for steering the rail. The guide may comprise a collar for example.

In other embodiments a support with a guide arrangement may be used with medical devices for percutaneous delivery other than a coaptation assist valve.

An alternative embodiment a device includes a support with a rail and a guide comprising a stylet and/or collar with a pre-formed bend which bends the support rail into the correct position. This fixed bend is straightened during delivery by passing through a larger/stiffer catheter. The fixed bend stylet/collar is useful where imaging prior to the procedure to assess the angle required; the axial position of the support rail can then be adjusted to optimise positioning. In a preferred embodiment, the radius of curvature of the support rail, collar and/or stylet will be small (typically from 3 mm to 30 mm). This enables the support rail to be guided around the limited space in the atrium. The support rail may also be guided by a pre-shaped collar or stylet that is additionally steerable.

The support may also be steerable at more than one point and/or pre-shaped. In another embodiment the support has a guide which is steerable at two separate points, and potentially steered with an offset of 900 between the two steering angles. Alternatively, the support may be steerable independently of a guide, for example using a pull wire associated with the support. In another embodiment the support is steerable at or near its distal end, and is used in combination with a steerable stylet or collar, the stylet or collar being slidable with respect to the support. More than one steerable stylet or collar may be used in combination with the support to fully orientate the conduit within the native valve. The location of the steering point on the steerable stylet or collar may be located at or near the distal end of the stylet or collar, but may be located at any location in the support.

The support collar and/or stylet can be made from polymer, metal, metal reinforced polymer tube, laser cut hypotube, laser-cut polymer tube, any combination of the above materials or any other suitable material. Preferably, the materials used will be suitable for long term implantation.

Figure 14:
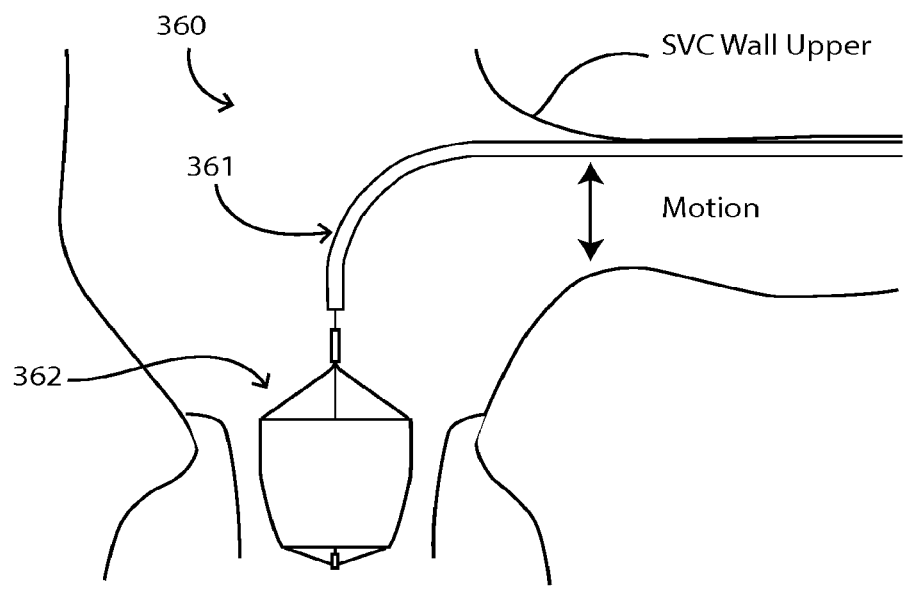
FIG. 14 shows how the conduit can experience large movement due to the large vessel size in the SVC (there can be significant motion of the support due to the large size of the SVC relative to the elongate support)
Figure 15:
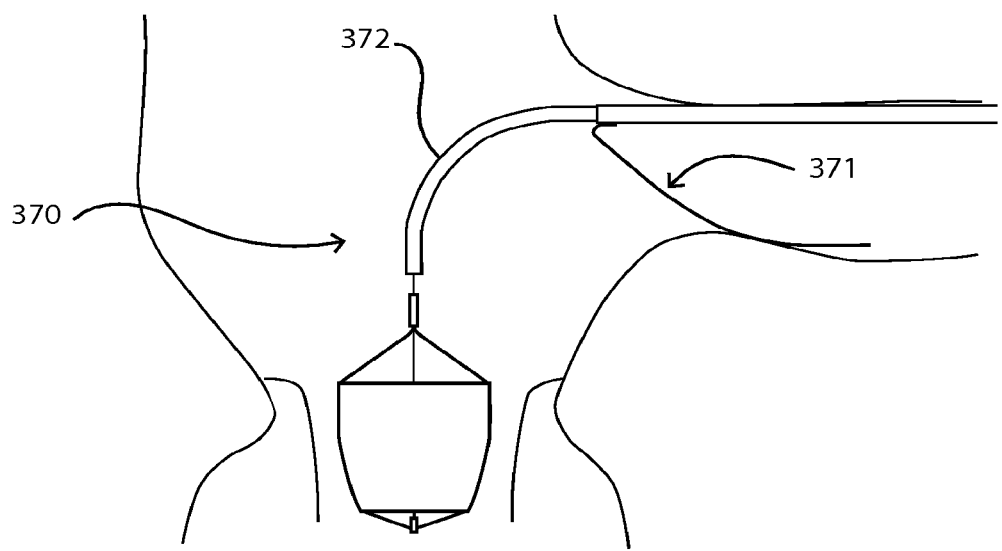
FIG. 15 shows how the introduction of a biasing element limits movement of the conduit.

Devices of various embodiments may include a "biasing" or "stabilisation" element to limit movement of the support. An example of this is shown in FIGS. 14 and 15. FIG. 14 shows that in a device 360 a support 361 can move substantially within the SVC and atrium for supporting a coaption assist valve 362. There can be significant motion of the support due to the large size of the SVC relative to the elongate support. A stabilisation element may be used to help position an elongate member within a vessel in any other apparatus.

FIG. 15 shows a device 370 having a stabilisation element 371 to press a support 372 against one side of the SVC, atrium or another vessel. In this case, the element 371 biases or pushes the support 372 to the upper side of the SVC.

The stabilisation element of FIG. 15 biases the support to the SVC wall (upper), limiting movement of the support. The stabilisation element is not limited to the example shown and can maintain the support into any orientation within the atrium, SVC or any other vessels that are larger than the support. The biasing shown in FIG. 15 involves use of only one element, but more than one element can be used. Biasing may be towards an extremity or towards a vessel centre, or anywhere in between. The stabilisation element may be circular or any suitable shapes, and may be made from shaped wire, or can be a stent or similar structure. The stabilisation element shown is separate and slidable relative to the support. However, the biasing may also be part of the support or the collar or stylet. It may also be rotatable with respect to the support, collar and/or stylet. The biasing element may be able to resist axial, rotational and/or radial motion. The support may be slidable and/or lockable relative to stabilisation element after deployment of the biasing element. The stabilisation element is configured to limit the movement of the coaptation assist valve or the "working" component of the device. The support may be arranged to be fixed to the stabilisation element.

Figure 16:
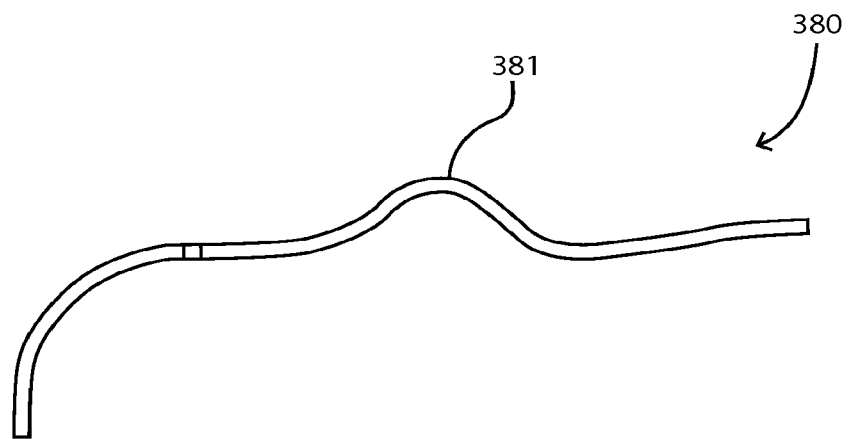
FIG. 16 shows an alternative biasing element in the form of a pre-shaped bump on the guide.

Another stabilisation means is a bend in the support so that it is shaped to maintain a desired position. One such example is shown in FIG. 16, which shows a support 380 with a pre-shaped "bump" or bend 381. This embodiment may contain one or more bumps or other eccentric characteristics. An alternative embodiment includes a pigtail shaped support for biasing. These features can be added to the support, guide and/or an independent element. Such elements can be used to steer as well as bias.

Figure 17:
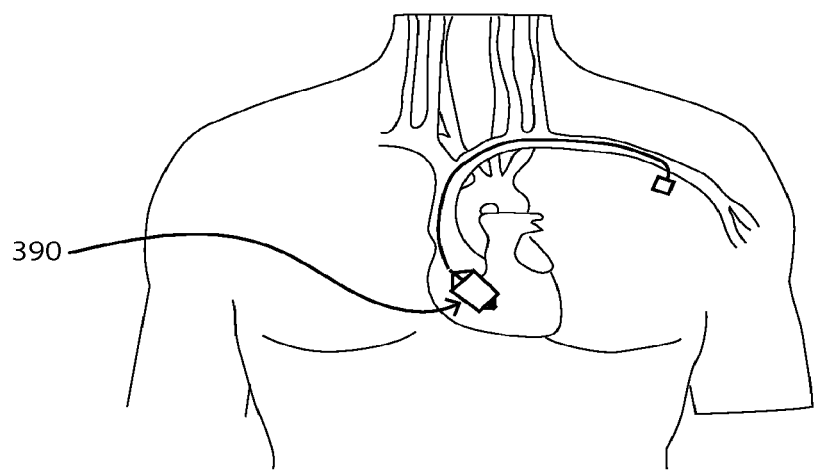
FIG. 17 shows the location of the fixation device outside the subclavian vein; this could also be located outside the jugular vein or any other vessel.

The support may be fixed by a stabilisation element at a location nearer the operator, such as but not limited to the subclavian vein. The support may be fixed within any vessel by a stent or similar structure or may be fixed outside the vessel. In the preferred embodiment, the support is fixed to the body by a stabilisation element (such as but not limited to a stent). In a preferred embodiment the stabilisation element is attached to a tube and the tubes are fixed together by a crimping or clamping element, either insider or outside the vessel. However, the stabilisation element may be attached directly to the support. The support may also be attached to the body outside of the vessel by methods such as suturing, or any other suitable method. FIG. 17 shows the location of a fixation position where the device is delivered through the subclavian vein. As mentioned, there are many alternative delivery paths for the device.

Figure 18A:
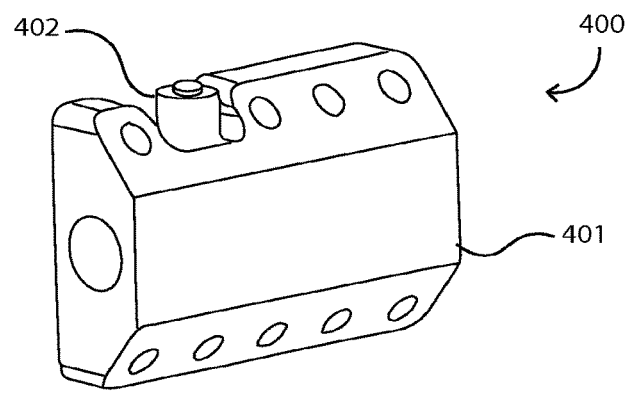
FIG. 18(a) shows a two-part fixation element, in which a first part can be fixed to the tissue by suturing in advance of positioning the support and once in position the second part is activated to lock the position of the support.
Figures 18B, 18C:
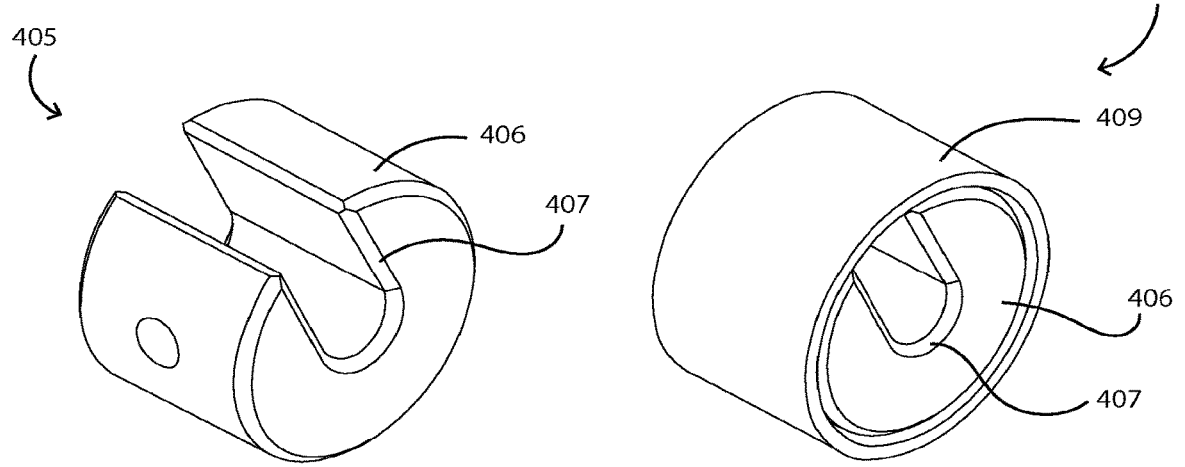
FIGS. 18(b) and 18(c) show a fixation element having an overall cylindrical shape, the latter having a bearing around the outside; these fixation elements being for limiting movement of the device after implantation; the second part of the fixation element is a screw with is screwed through a hole.

The support may be fixed by any type of clinical procedure that is known such as suturing, mechanical fixation or any other type. The preferred fixation mechanism is a multiple part fixation device, and FIG. 18 shows an example of this. This example is used where the device is attached to the body by a stabilisation element such as a stent, and the stent is attached to a tube. Once a suitable position is found, the part is placed over all tubes and a screw delivered through the hole (please label) to fix all tubes together. The part can optionally be fixed to the body with sutures or another method. In preferred embodiment fixation element 406 is not fixed to the body. A further example of this includes the addition of a bearing element 409 around this. Where the bearing element contacts the body and prevents motion, the fixation element 406 is free to rotate. An additional element to this includes lengthening the bearing element such that the fixation element 406 is free to rotate within the bearing 409 but also has a limited amount of freedom of axial movement. FIG. 18(*a*) shows a support fixation stabilisation element 400 having at least two parts. In the shown example, a part 401 can be fixed to the tissue prior to fixing support, for example by suturing to fatty tissue, muscle or bone. The support and/or anchor can then be positioned within a fixation and a part 402 can fix the support and/or anchor to the fixation part 401; in the shown example, part 402 of the fixation is a grub screw. The fixation device may alternatively be circular in profile to prevent rotation due to contact with tissue, but may also be non-circular to control rotational movement.

Referring to FIG. 18(*b*) a fixation element 405 has a predominantly circular profile in cross-section with a cylindrical outer surface 406 and a channel 407 for an elongate support to minimise rotation of the element with tissue contact; rotation of the fixation element can translate to rotation of the conduit.

Referring to FIG. 18(*c*) in a fixation element 408 there is a circular bearing-like element 409 surrounding the cylindrical surface. This ensures that with tissue contact the fixation element is free rotate; this can aid embodiments of the device where the fixation element only fixes elongate elements together and doesn't engage with tissue from the body. The fixation element in FIGS. 18(*b*) and (*c*) may not be fixed to the body.

The stabilisation element or fixation device may take many forms, such as but not limited to, the above embodiments, interference fits, crimps, rivets, clamps compression joints etc. It may be located at the operator site or more distally towards the biasing element, and/or more distal than the biasing element. There may be one of more fixation devices which may be the same or different. The fixation device may fix one or more elements together.

Figure 19:
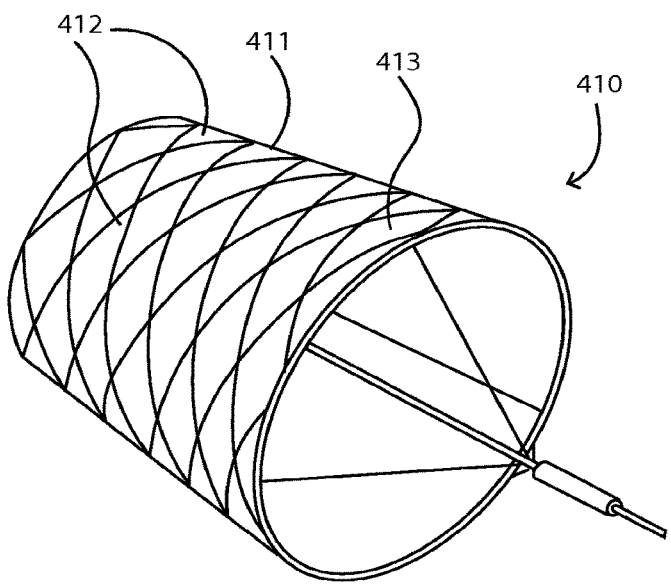
FIG. 19 shows the conduit made from a composite material, in this case a braided laser cut metal (or polymer), with an infill of silicone flexible material; alternatively a material such is silicone or pericardium could be fixed to, around or within the braided/laser cut structure.
Figure 46A:
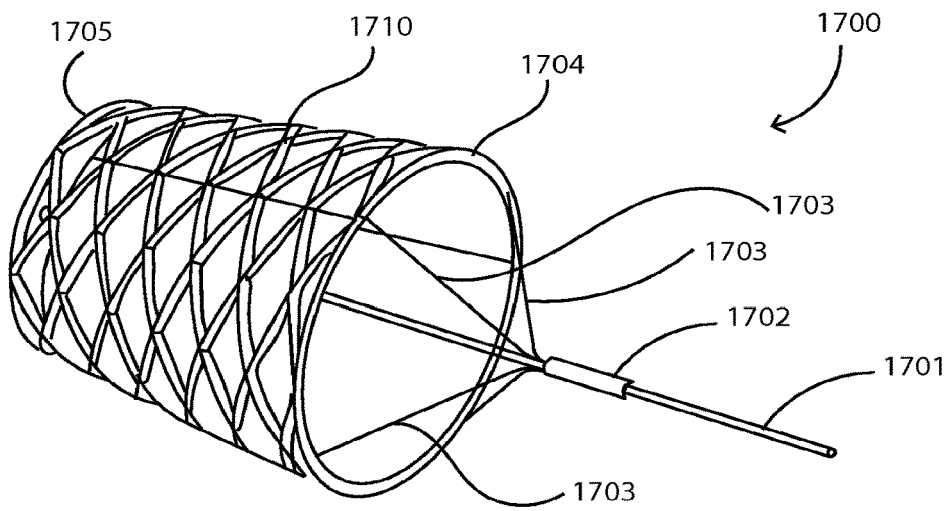
FIG. 46(a) shows an uncovered braided/stented structure of conduit side wall.
Figure 46B:
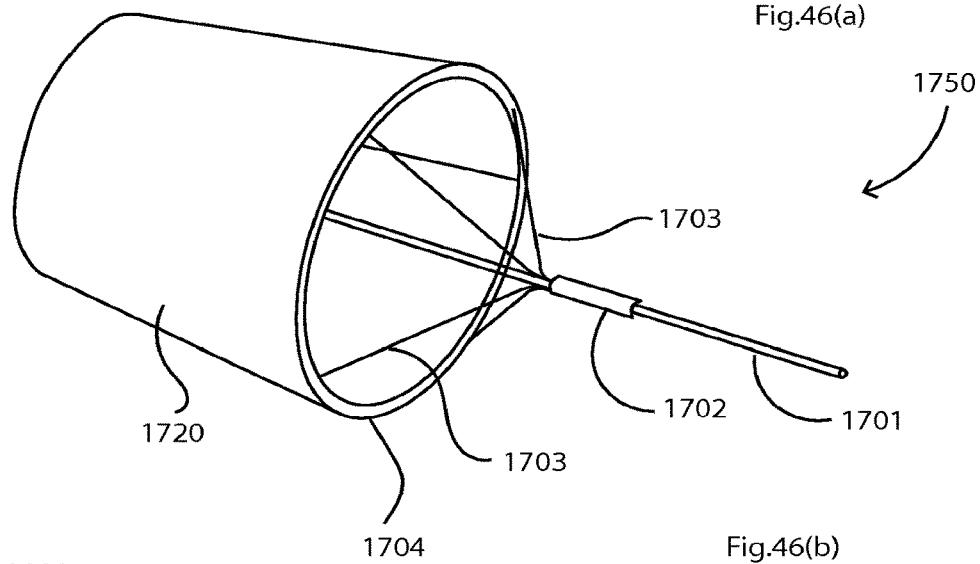
FIG. 46(b) shows it with a cover of material such as pericardium tissue.

In other embodiments the conduit comprises a compliant material such as pericardium, but may alternatively or additionally comprise rigid or semi rigid materials such as metals or polymers. The conduit may comprise a composite material, such as a braided or laser cut metal or polymer. This may have an infill of a flexible material such as silicone, so that it can be collapsed to a small diameter for delivery while maintaining structure after delivery (FIG. 19). Alternatively, the conduit may be a stented or partially stented structure, optionally covered in a material such as pericardium. FIG. 46(*a*) shows a stented frame and FIG. 46(*b*) shows the stented frame covered in pericardium. This facilitates the conduit and valve structure while also providing a soft surface for coaptation. The frame can take many forms and be formed from braided polymer or metal wire, from laser cut tube or another method known by those skilled in the art. The frame may also have longitudinal struts for easy valve attachment.

FIG. 19 shows a coaptation assist valve 410 in which a conduit 411 is made from a composite material, a braided mesh (in other embodiments laser cut metal or polymer mesh) 412, with an infill 413 of a flexible material such as silicone. The conduit may have a circular, triangular, oval or other cross section to suits the regurgitant orifice. The cross-section of the coaptation surface may be circular but may alternatively be oval, triangular or any other suitable shape for coaptation with the native leaflets. The conduit may be cylindrical, conical, including a truncated cone, balloon shaped, oval in the long axis of any other shape. In other embodiments, the diameter/circumference of the distal end may also be larger or the same as the proximal end.

Figure 20:
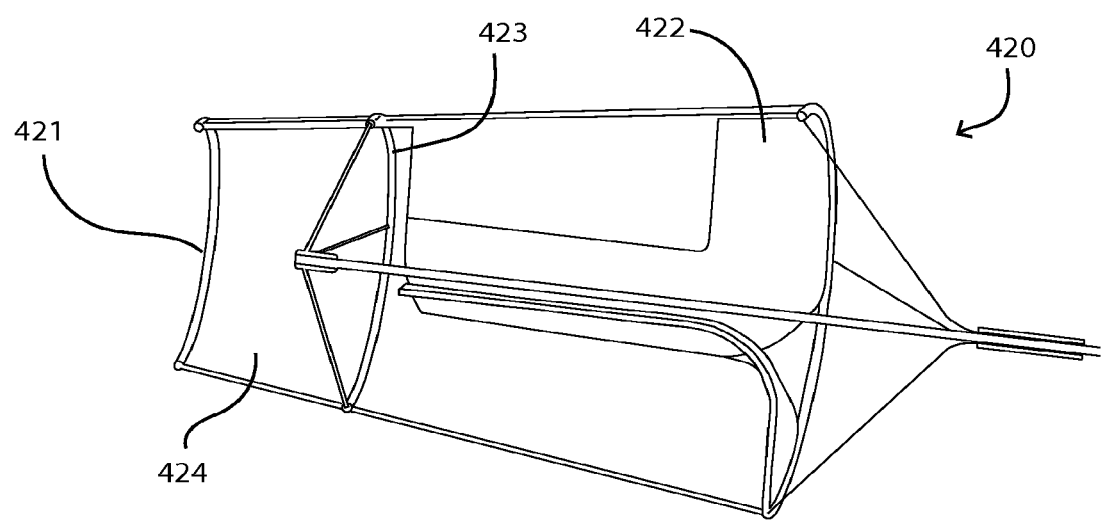
FIG. 20 shows the conduit with an additional ring distal to support the conduit, to prevent the tip from extending distally of the coaptation surface.

FIG. 20 shows a coaptation assist valve 420 in which an additional ring 421 is distal of the valve 422 and a first distal ring 423, to prevent trauma caused by the tip (distal end of the support). Effectively, this provides for a continuation of the conduit to act as a shield 424 around the distal end of the support.

Figure 21:
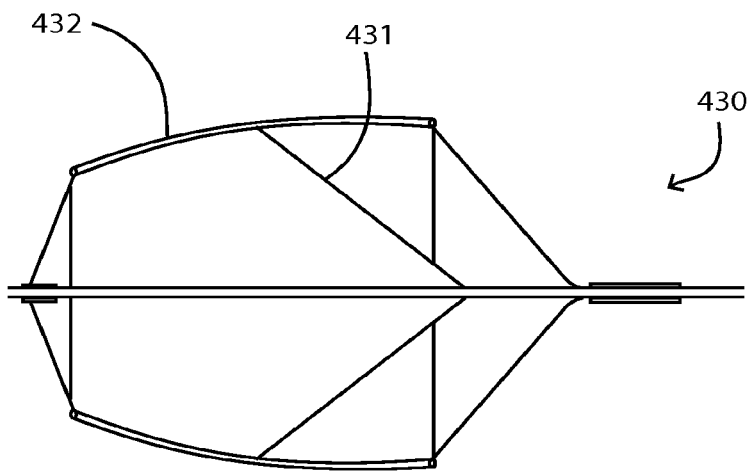
FIG. 21 shows the conduit with a valve that opens out from the central support.

FIG. 21 shows in a coaptation assist valve 430 having a prosthetic a valve 431 which opens out to meet an inner surface of the conduit rather than closing in to meet support.

Figure 22:
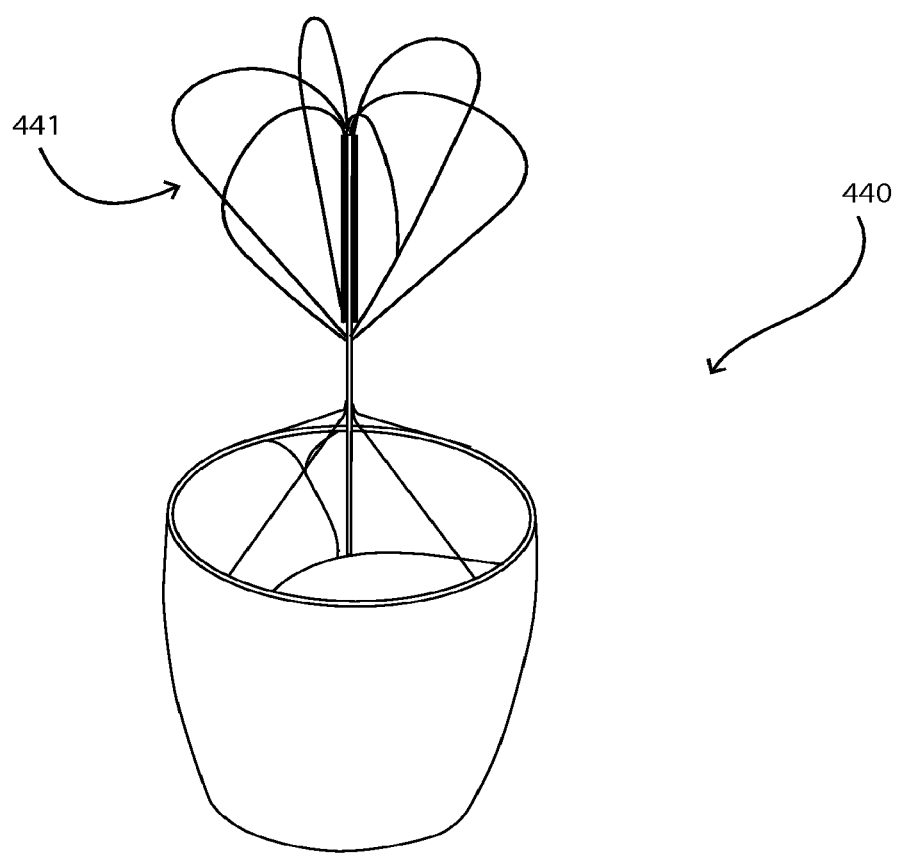
FIG. 22 is a perspective view showing proximal wings which may anchor the valve in the atrium.

FIG. 22 shows in a coaptation assist valve 440 supported by a support having proximal wings 441 which anchor the element 440 in the atrium, with the use of an atrial basket, stent or shaped wire, on the basis of a Mitramaze spacer for mitral regurgitation (Espiritu et al, *Annals of Biomedical Engineering*, February 2017, Volume 45, Issue 2, pp 332-359). This type of system could be used in conjunction with a steerable element to position the coaptation assist valve.

Figure 23:
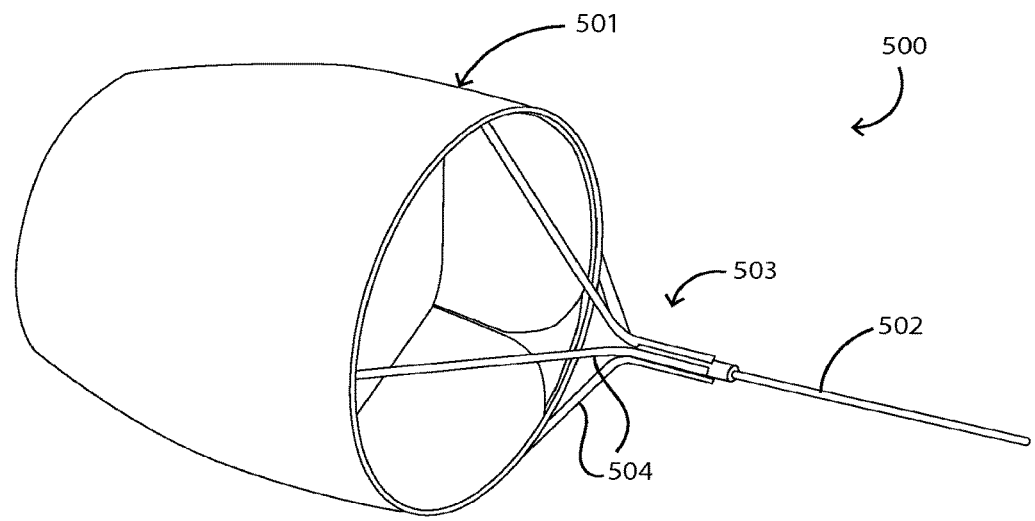
FIG. 23 is a perspective view showing a device having a rail which terminates on the proximal side of the conduit and valve.

The support may be connected only to the proximal side of the coaptation assist valve (FIG. 23) and not pass through the coaptation assist valve. Referring to FIG. 23, a device 500 comprises a coaptation assist valve 501, a support 502, and fixation connectors 503 between the coaptation assist valve and the support including tethers 504 extending distally of the rail 502. In this case the support does not extend through the coaptation assist valve. The support may extend partially through the coaptation assist valve; in the preferred embodiment the support extends partially through the conduit but does not pass through the coaptation region of the valve leaflets.

Figure 24:
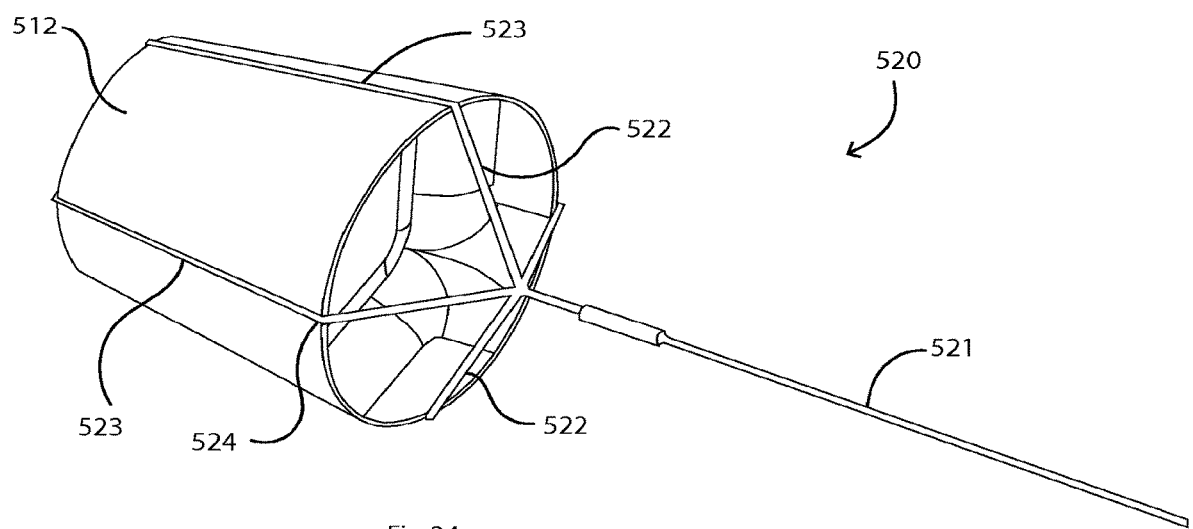
FIG. 24 shows a conduit, in which the support maintains the conduit in position from the proximal end only (parts labelled 513 are now continuous)

The support may not pass through the coaptation assist valve and may support the proximal structure, or both the proximal and distal rings. FIG. 24 shows a device 520 with a support 521 connected by rigid tethers 522 to both the proximal and distal rings, not passing through the valve element but rather surrounding it. In this embodiment, the support 521 and 522 provides a connection to the rings, and also structure between the rings, because of the configuration in which it extends radially at the proximal end of the valve element and then longitudinally as struts 523 along the surface of the conduit 512 in the form of stiffening ribs.

Figure 25:
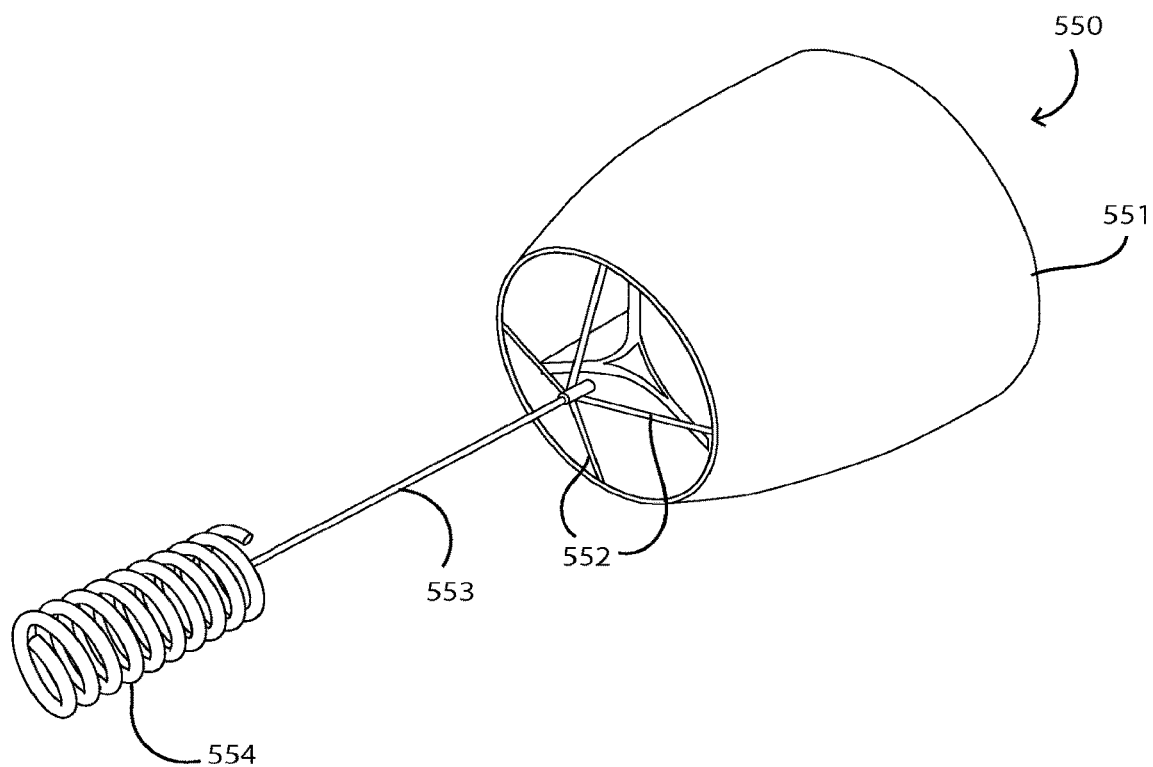
FIG. 25 is a perspective view showing a device which is supported by a distal rail with a corkscrew fixation to the ventricle wall, in which the rail terminates on the distal side of the conduit and valve.
Figure 26:
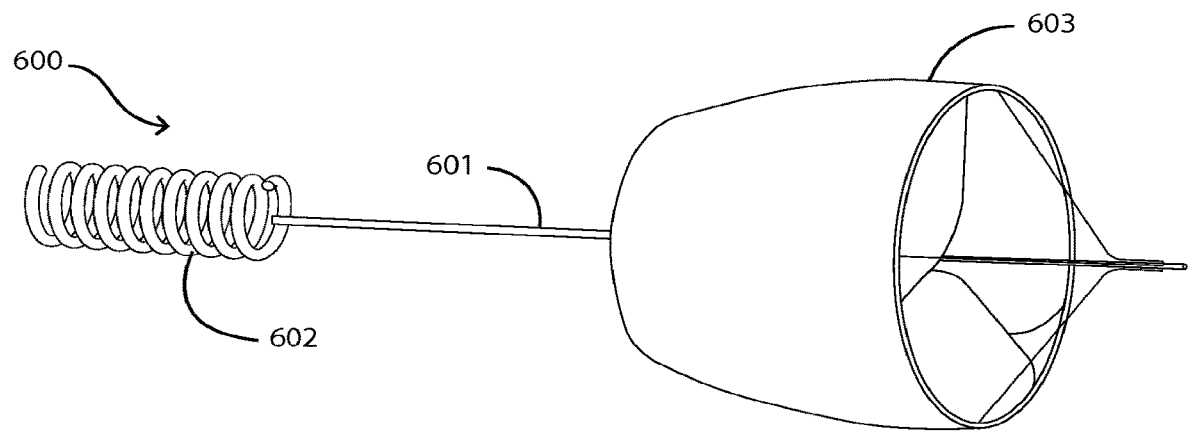
FIG. 26 is a perspective view of a device which is supported by a rail which extends axially through the conduit and valve and has a distal corkscrew fixation to the ventricle wall.

The support may be fixed to the body distally of the conduit (FIG. 25), such as fixed to the ventricle or other vessels connected to the ventricle. In this case a device 550 has a coaptation assist valve 551 linked by tethers 552 to a distal rail 553 having a distal anchor 554 in the form of a corkscrew for engaging ventricle tissue. In another embodiment, in a device 600 shown in FIG. 26, a support 601 is fixed to the ventricle wall by a corkscrew anchor 602 and extends proximally through a coaptation assist valve 603; in this case the coaptation assist valve is attached to the support with both distal and proximal tethers. The support in this embodiment is attached to the ventricle using a corkscrew, however, other means of fixation may be used. In these embodiments the device does not have the benefit of the suspended support arrangement, but would have advantages arising from the features of the coaptation assist valve.

Figure 27:
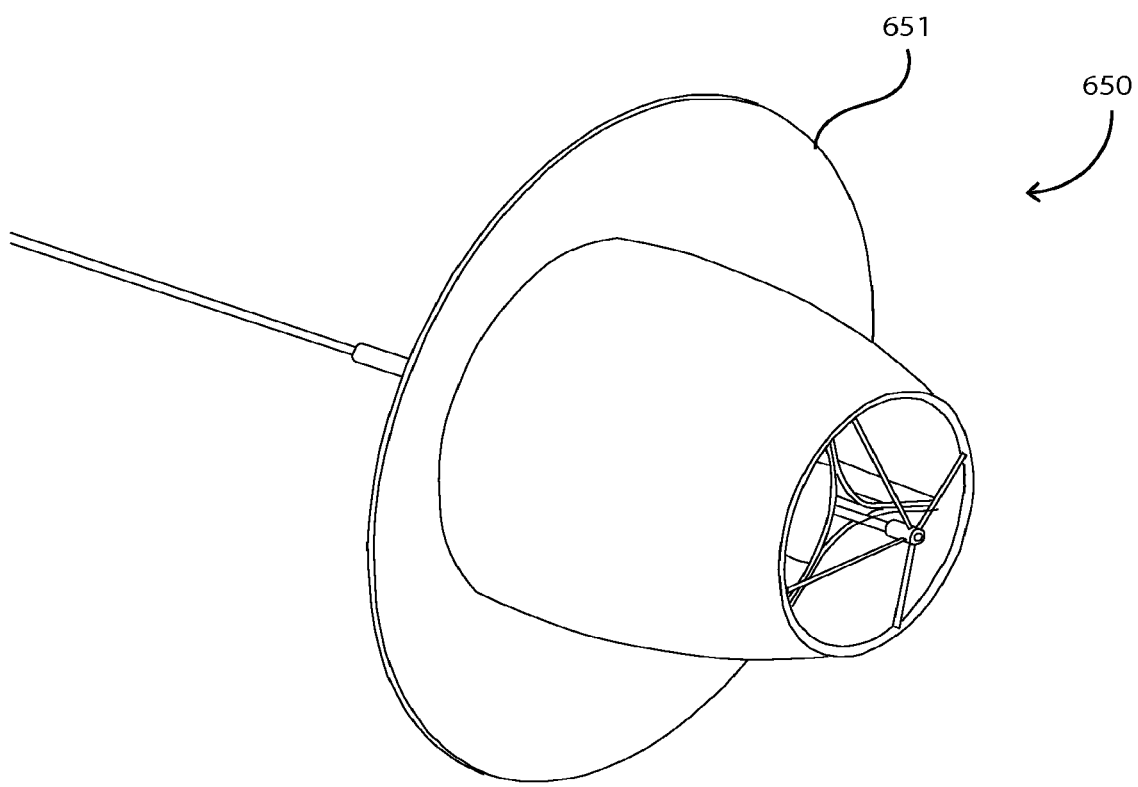
FIG. 27 shows a conduit with a flange that can integrate with the native valve annulus.

An alternative embodiment includes the coaptation assist valve (650 in FIG. 27) containing a flange 651 that can be arranged around the coaptation assist valve. This flange may be in contact with the annulus of the native valve and may embed into the annulus over time. In this case, the support may be removable from the body. The flange may also allow for both radial and longitudinal coaptation.

Figure 28:
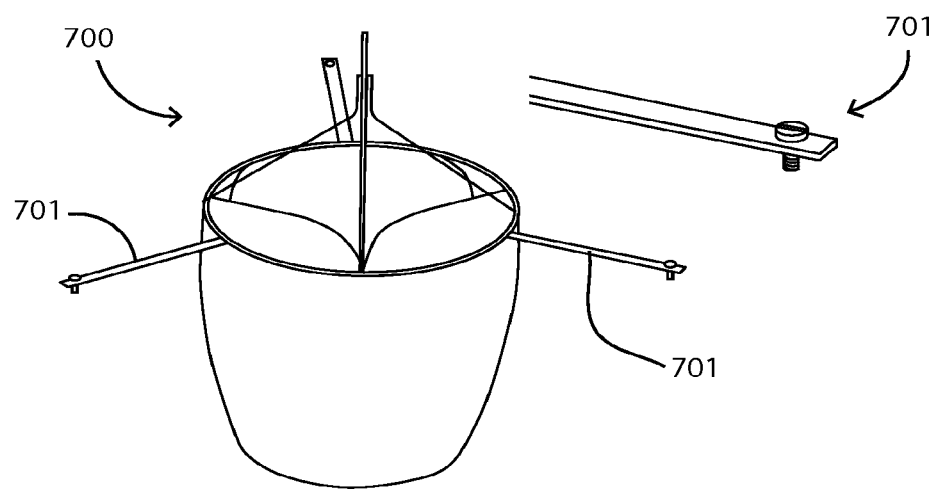
FIG. 28 shows a conduit with additional supports that can screw into the native valve annulus; alternatively, the screws could be replaced by corkscrew elements.

A further embodiment includes a valve 700, an attachment of one or more supports 701 extending radially for attachment to the native annulus (FIG. 28); screws, clamps sutures, corkscrew elements or other mechanical fixing methods may be used to attach to these supports to the native annulus.

Figure 29:
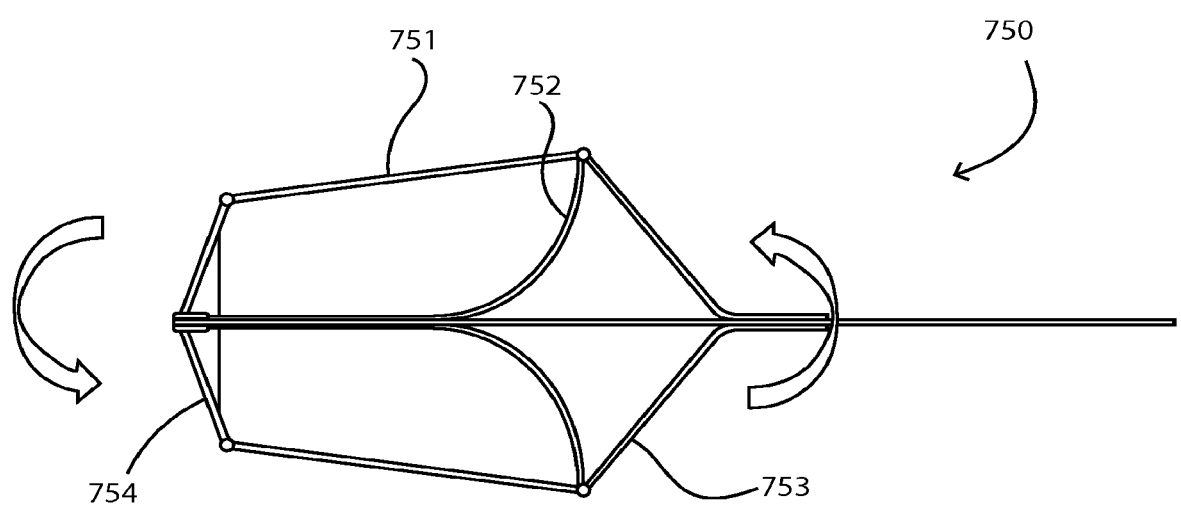
FIG. 29 shows how distal and/or proximal tethers may be flexible to allow the valve element to pivot about the support (distal and/or proximal tethers may be flexible to allow coaptation assist valve to pivot about the support)

FIG. 29 shows how distal and/or proximal tethers may be flexible to allow the coaptation assist valve to pivot about the support. This device, 750, comprises a conduit 751 having a proximal rim supporting a prosthetic valve 752. There are both proximal and distal tethers 753 and 754, both of which are flexible.

The support may also be flexible at one or more locations to allow the conduit to self-centre within the native leaflets. One such example of this is a universal joint immediately proximal to the conduit to allow the conduit to pivot and orientate itself. A universal joint more proximally may also allow the support to bend and self-centre within the native valve. A flexible section of the support, or another mechanism known to one skilled in the art, could also achieve the samue results as a universal joint. There may be one or more pivot points within the support.

The support may include one of more of the components of the above embodiments. For example, the support may be flexible and be steered into position by a steerable guide, and then reinforced by a stiff stylet. Optionally, the support is hollow to allow the use of a guidewire, stylet or for delivery of a pacemaker lead or other lead. There may also be additional concentric or non-concentric cavities in the support or coaptation assist valve for delivery of pacemaker leads or other therapeutic devices. The support may be concentric or eccentric to the coaptation assist valve.

All embodiments mentioned in this document may be used over a guidewire. Some or all of the parts in the above invention are implantable and may also be retrievable.

Figure 30:
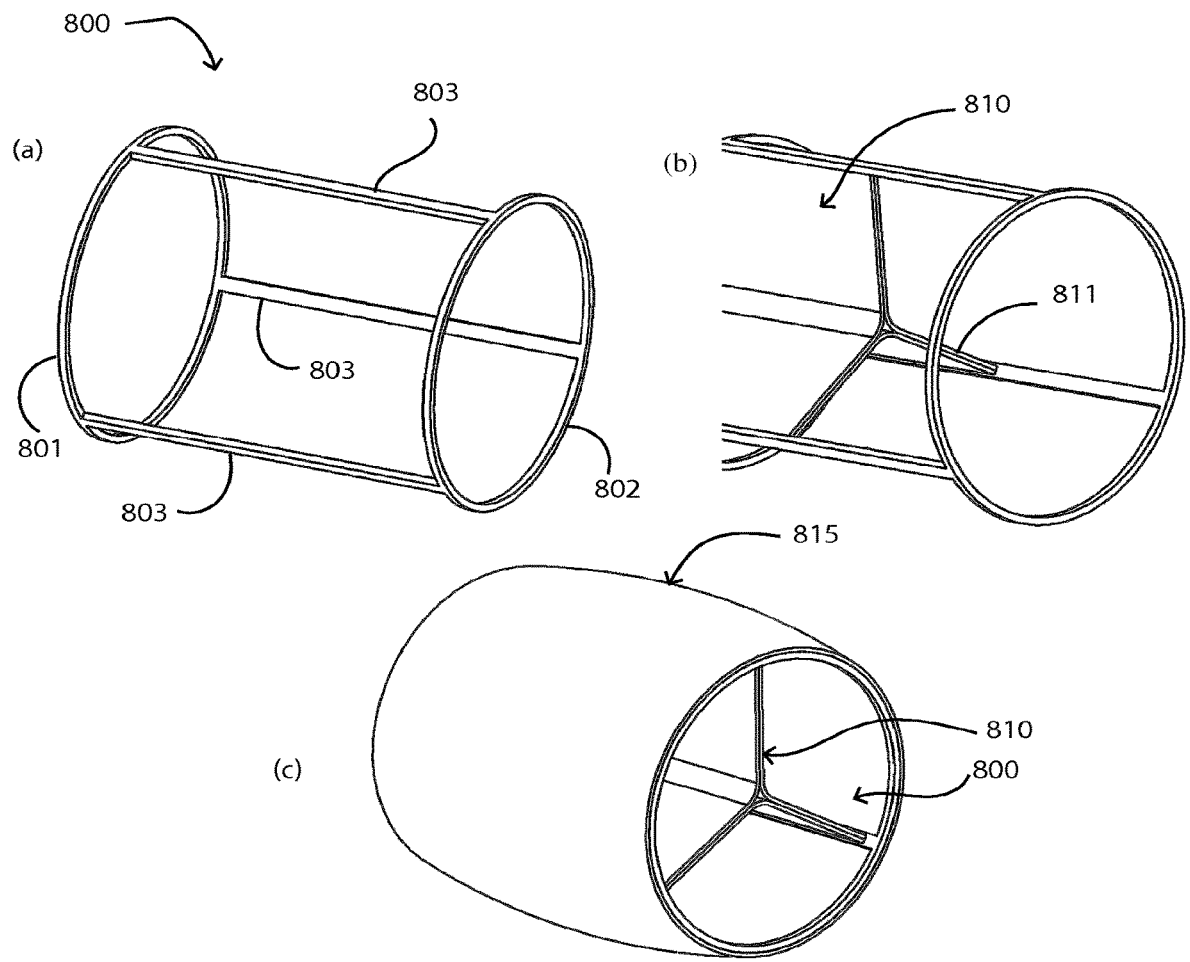
FIG. 30 is a set of perspective views showing (a) a frame with distal and proximal rings attached by longitudinal struts, (b) longitudinal struts being used to support the valve leaflets, and (c) a conduit being assembled over the frame and attached to the distal ring, proximal ring and/or the longitudinal struts.

The coaptation assist valve structure may comprise a single frame which includes both distal and proximal ends. An example of this is shown in FIG. 30, in which a frame 800 includes distal and proximal rings 801 and 802 attached by longitudinal struts 803. FIG. 30(*a*) shows the frame 800, and FIG. 30(*b*) (top right view) shows leaflets 810 fixed inside the frame longitudinal struts 803. A conduit side wall 815 is attached to the outside of the frame (FIG. 30(*c*)). Preferably, the conduit side wall is attached only to the distal and proximal ends, but may also be attached to part or all of one or more of the longitudinal struts. There may be one or more longitudinal struts; preferably there will be three.

Figure 31:
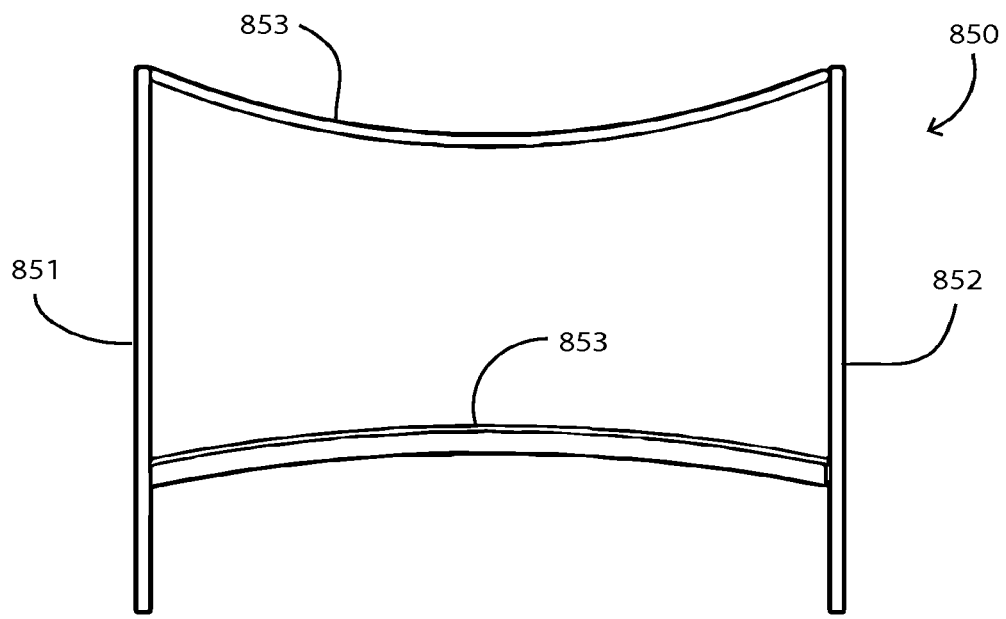
FIG. 31 shows a variation with curved longitudinal struts.

As shown in FIG. 31, a conduit frame 850 may have distal and proximal rings 851 and 852, but the longitudinal struts may be curved (853) to prevent contact with the conduit sidewall. Similarly, they may be tapered inwardly to avoid this contact.

Figure 32:
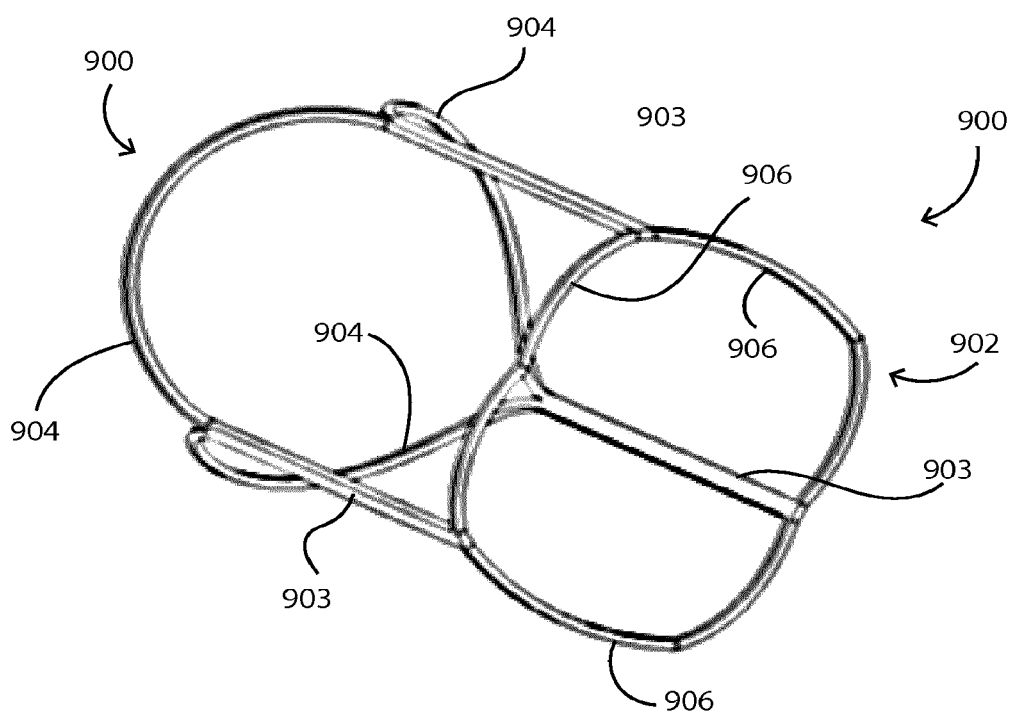
FIG. 32 shows a frame with a scallop-shaped support at one end to facilitate attachments of leaflets, the other end formed by V-shaped members.

As shown in FIG. 32, a frame 900 may have an end 901 with a "scallop" shape, 904. This facilitates better leaflets function, flow characteristics and wear profile. The frame 900 also has three V-shaped members 906. This is particularly suitable for crimping and expanding the frame. The scallop shape may be at the distal and/or proximal ends or between the distal and proximal ends. Similarly, the V-shape may be located at either the distal and/or proximal end, or between the ends. Each element, with V-shaped (906) or arc-shaped (904) is joined at each end of an end of a longitudinal strut 903, of which there are three extending between the ends 901 and 902.

Figure 33:
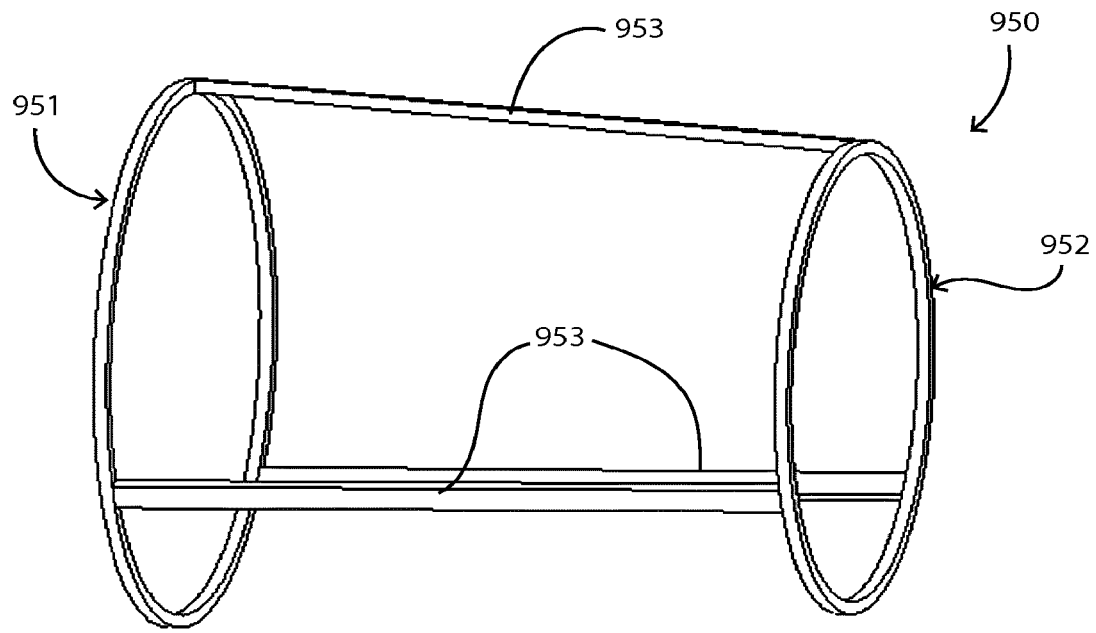
FIG. 33 shows a frame with an overall tapered shape, having a smaller-diameter ring at one end than at the other.

FIG. 33 shows a conduit frame 950 which is tapered in its overall outline. It comprises a proximal ring 951 and a smaller-diameter distal ring 952 joined by longitudinal struts 953. The frame may alternatively have a larger diameter at the distal end than at the proximal end.

Figure 34:
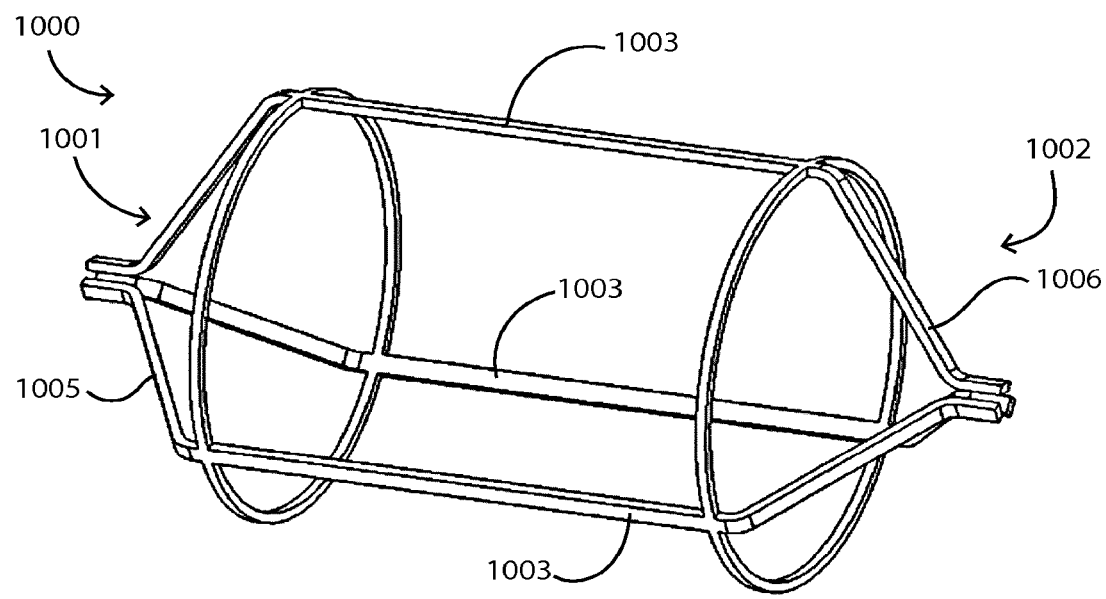
FIG. 34 shows a frame with rigid tethers at each end for connection to a support.
Figure 35:
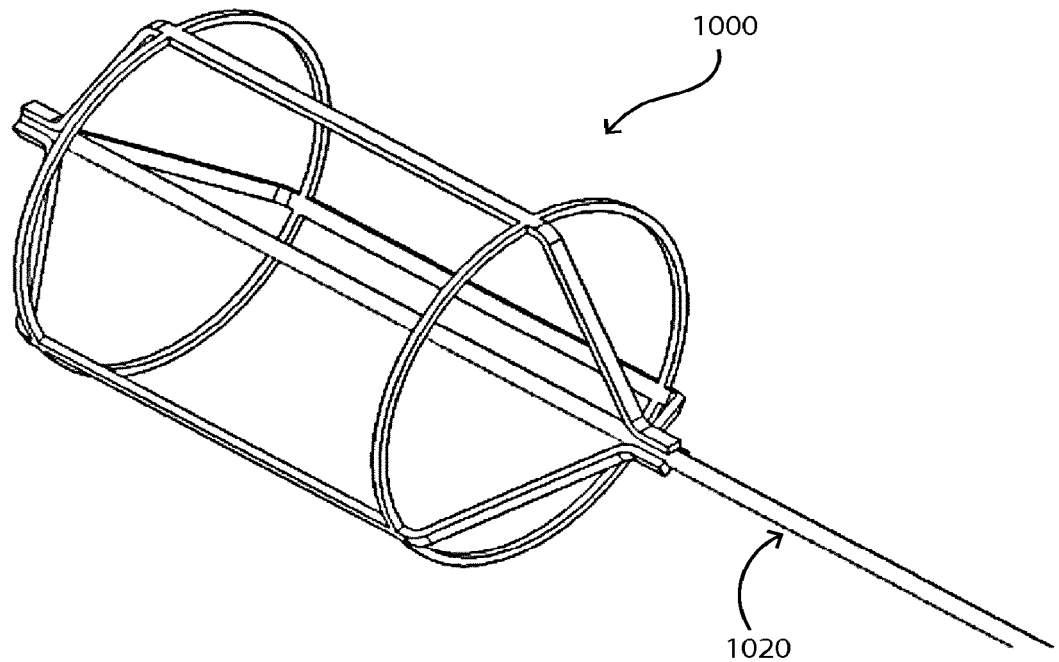
FIG. 35 shows a frame connected to a support using both distal and proximal rigid tethers.

Referring to FIG. 34, a conduit frame 1000 comprises an equal ring 1001 and 1002 at each end joined by longitudinal struts 1003. Rigid or semi-rigid tethers 1005 and 1006 are provided for connecting the frame to a support. In various embodiments, the frame may have any combination of rigid and flexible tethers at the distal and proximal ends. The tethers may be connected at any points around the circumference of the frame, and at any point between the distal and proximal ends. For example, the tethers may branch from the longitudinal struts between the distal and/or proximal ends FIG. 35 shows a frame 1000 attached to a support rail 1020 by rigid distal and proximal tethers.

Figure 36:
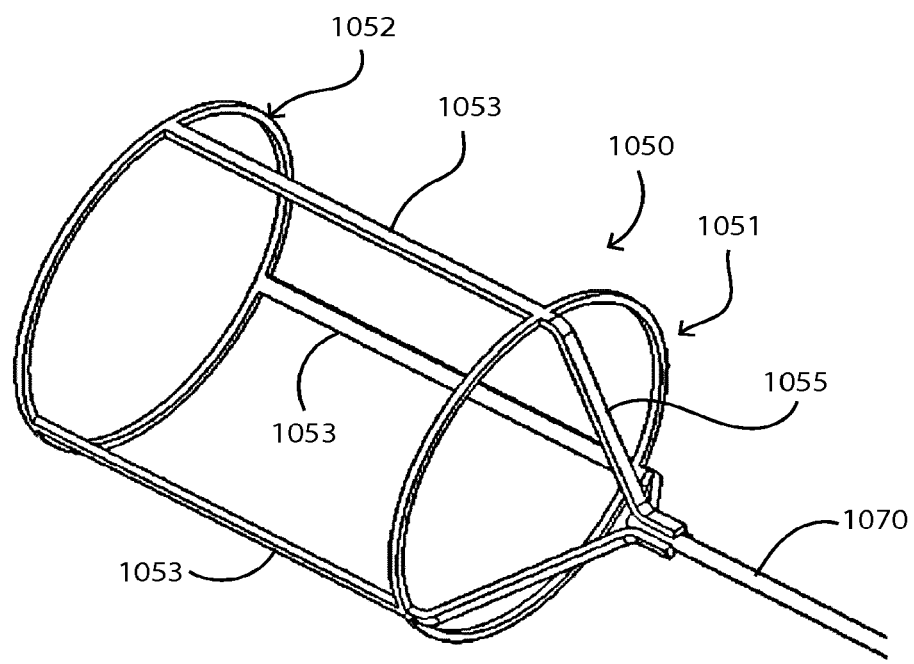
FIG. 36 shows an alternative frame, having rigid tethers at one end and no tethers at the other end, and fixed to the support at the end with tethers.

The frame may be attached with only distal or proximal tethers. There may be further tethers between the distal and proximal ends, and the support may extend only partially through the frame or only to one end. There may be separate distal and proximal structures which may comprise a frame and/or rings. There may be more than two structures connected to the support. For example, as shown in FIG. 36 a frame 1050 has rings 1051 and 1052 at the ends joined by longitudinal struts 1053. There are tethers 1055 at one end only, shown joined to a support 1070. In this case the support does not protrude into the volume of the frame.

Support with Guide

In various embodiments the support has a guide having structural integrity to guide the coaptation assist valve into the correct direction and/or position. The support with a guide may also have sufficient stiffness to maintain the coaptation assist valve in the correct direction and/or position. Such a support may comprise a steerable catheter, such as that with a pull wire, which applies tension to at least one eccentric location on the catheter, bending it in that direction.

In one embodiment, the support is arranged to straighten an elongate element such as a catheter, pre-shaped wire, tube or other shape. This has the benefit of reducing the force required to create a large bend in the elongate element for implantation.

Figure 37:
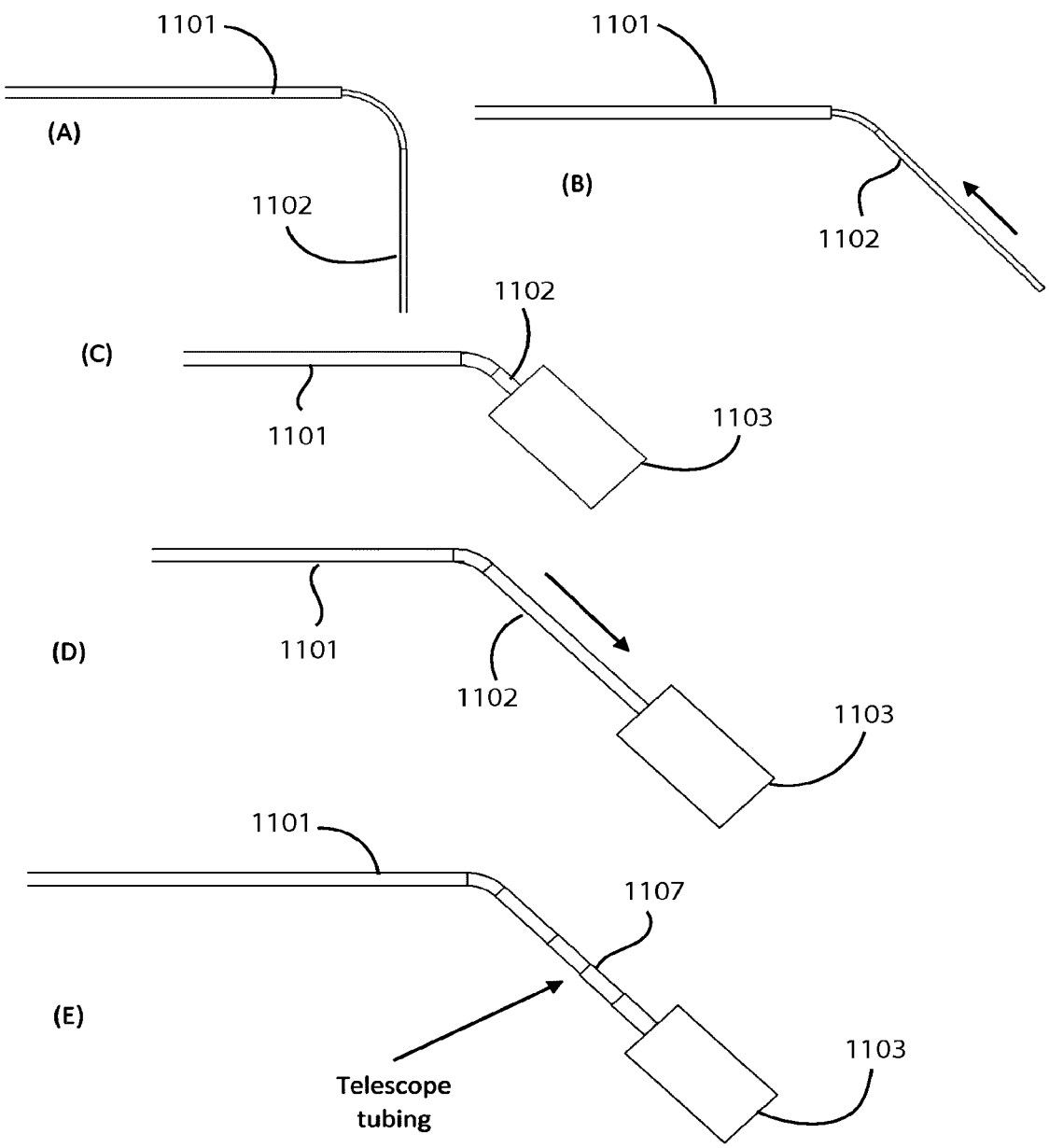
FIG. 37 shows a guide for steering the support, (a) shows a pre-shaped wire within a stiff catheter (1101); (b) the pre-shaped wire is withdrawn into the stiff catheter, straightening/steering the pre-shaped wire; (c) shows a coaptation member attached to a catheter; (d) shows the catheter being advanced relative to the bend; and (e) shows that further extension can be achieved by adding telescoping elements.

In one embodiment, the steerable guide is made from straightening a pre-shaped wire, tube or other shape. This has the benefit of reducing the force required to create a large bend in the catheter for implantation. FIG. 37 shows a guide as an example of this, with a pre-shaped wire mandrel 1102 as a rail inside a stiffer tube 1101 (FIG. 37(*a*)). The wire 1102 is preferably of Nitinol. Pulling the wire 1102 proximally (or pushing the tube 1101 distally) deflects the wire into a straighter direction (FIG. 37(*b*)). In addition to this, another tube 1103 with a valve to be deployed is passed over the deflected wire 1102 leaving only a short exposed portion of the wire 1102, with advancement of this tube 1103 moving the axial position relative to the bend (FIGS. 37(*c*) and (*d*)). This is particularly beneficial where there is a known large deflection range required. It is also useful in that it steers the guide only at the location of the pre-formed bend.

FIG. 37(*e*) shows that a telescopic tube 1107 may protrude from the guide tube 1101, as another way to adjust position of the valve 1103.

In one embodiment, the coaptation assist valve is placed on the member which is advanced relative to the bend. The coaptation assist valve can then be directed toward the centre of the native valve by the combination of the shaped wire and the stiffer tube and advanced across the native valve. All parts may be made from wires or tubes or alternate shapes and may alternate in order from centre to periphery. Preferably, elements will be concentric but it is not essential. The shaped mandrel can be located in a single or multi-lumen tube. As the support is advanced, the coaptation assist valve can become unsupported from the steerable catheter. The support may contain a stiffer distal section (such as a steel tubular section) to ensure its stability. Additionally, multiple stiffer tubes could be used to create a telescope-like effect (FIG. 37(e)). The guide is implantable in a preferred embodiment. The guide may have variable properties along its length. These variable properties could include: material choice, material properties, and geometry. A coaptation member that doesn't include a valve may also be used.

Referring to FIG. 38, a stabilisation element 1120 comprises a stent with longitudinal struts 1121 and circumferential hoops 1122 with peaks. This has the advantage that the support (1100) is biased towards a wall of the vessel, while also resisting axial motion of the support and coaptation assist valve. The stent is attached to the steerable catheter and/or to the support (FIG. 38(a)). In one embodiment, the stent is attached to a separate tube, such that axial and rotational movement of the support is enabled relative to the stent (FIG. 38(b)). The support may be rotatable or fixed with respect to the stent. The stent may also include longitudinal bars to facilitate attachment of a tube to the stent, preventing lengthening and shortening of the stent at the tube connection. The stent may also be detachable from the tube from a variety of methods, such as unclipping, release mechanism, designed break points or any other mechanism know to those skilled in the art. The stents may be balloon expandable, self-expanding, bioresorbable or any other type of known stent.

The stent may have hoops that form V-shapes in a zig-zag pattern. These hoops may be orientated in a single orientation (FIGS. 38(a) and (b) and FIGS. 39(a) and (b)), or orientated in two directions (1151, FIG. 39(b)) or various combinations of these, such as diamond shapes.

Figure 39C:
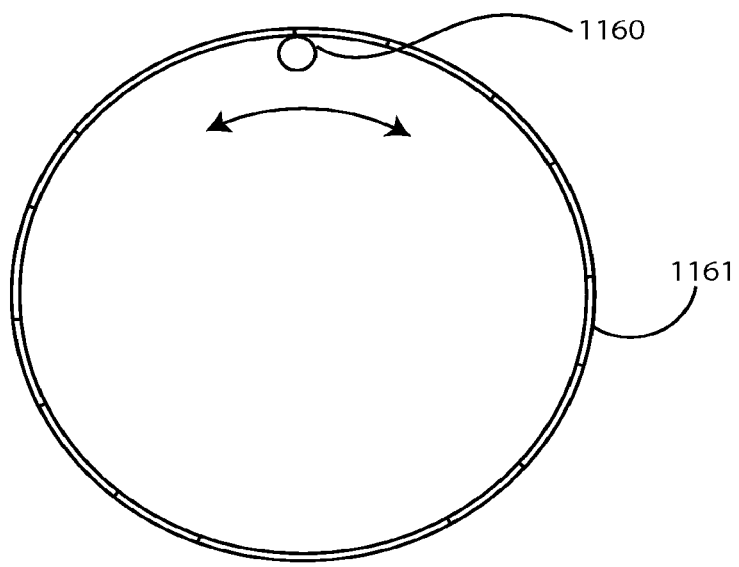
FIG. 39(c) shows how rotation of the stent can bias the support to different positions in the vessel.

FIG. 39(c) shows how a stent-like stabilisation element 1161 holds a support 1160 along the radial extremity and hence biases the overall support radially. However, by rotation of the element as indicated by the arrows, the anchor 1160 may be biased against the opposite side, or anywhere in-between.

The orientation of these hoops has a significant effect on resisting motion of the stent. The stent may also be tapered in diameter to accommodate the changing anatomy along its length. The radial force may also be variable along its length to accommodate changes in anatomy or material characteristics required. These hoops may also be tapered inward towards the centre of the vessel, facilitating irretrievability of the device using hooks or equivalent.

Figure 40:
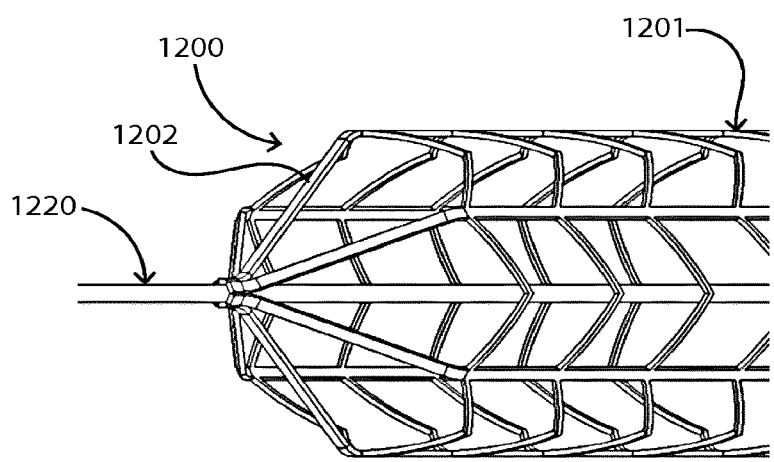
FIG. 40 shows a stent arranged to retain the support rail centrally in a blood vessel.

In one embodiment, the stent-like stabilisation element biases the support towards a wall of the vessel in which it resides. However, as shown in FIG. 40 an element 1200 may alternatively bias the support 1220 towards the centre of the vessel, or anywhere between the wall and the centre. The element 1200 may also have bars 1202 attaching it to the support to enhance retrievability. The element can be orientated around the full periphery of the vessel to improve positioning and/or stability. There may also be more than one stent on the vessel, which can stabilise all or part of the support length. The stent-like elements may be laser cut, but various other manufacturing methods may be used, such as braiding wire, or using one or more undulating shaped wires.

It will be appreciated that the device allows standard procedures and techniques to be used such as those used during pacemaker lead implantation. This approach will ensure safety, ease of use and a high physician adoption rate. The implant can be readily placed in the correct position to inhibit regurgitation of the tricuspid valve. The device can not only treat tricuspid valve disease but be used to treat other AV valves.

Figure 41:
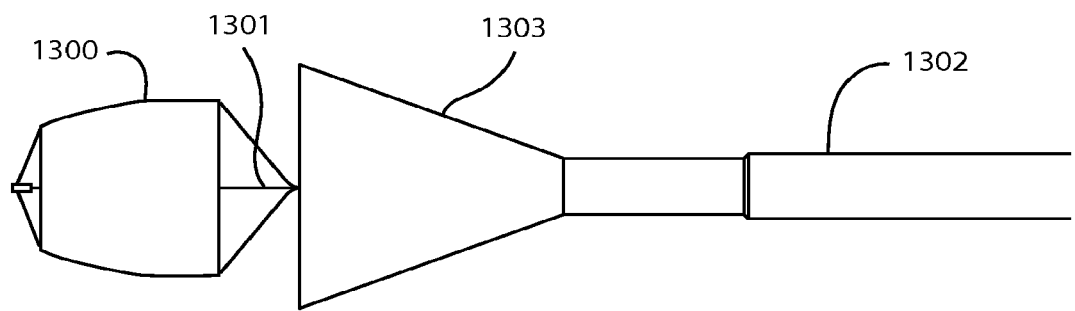
FIG. 41 is a side view showing a flared element at the distal end of a catheter for full or partial retrieval of a conduit.

As noted above, some or all of the parts are implantable, and may also be retrievable. For example in FIG. 41, the conduit 1300 may be pulled into a flare 1303 and collapsed into a sheath 1302. Alternatively, the conduit 1300 may be partially pulled into a flare 1303, and both the flare and device pulled together into another catheter sheath 1302. Another embodiment includes having a flare on the introducer. Many other methods of retrievability may be undertaken, including detaching the conduit, and snaring it from another access site.

Figure 42:
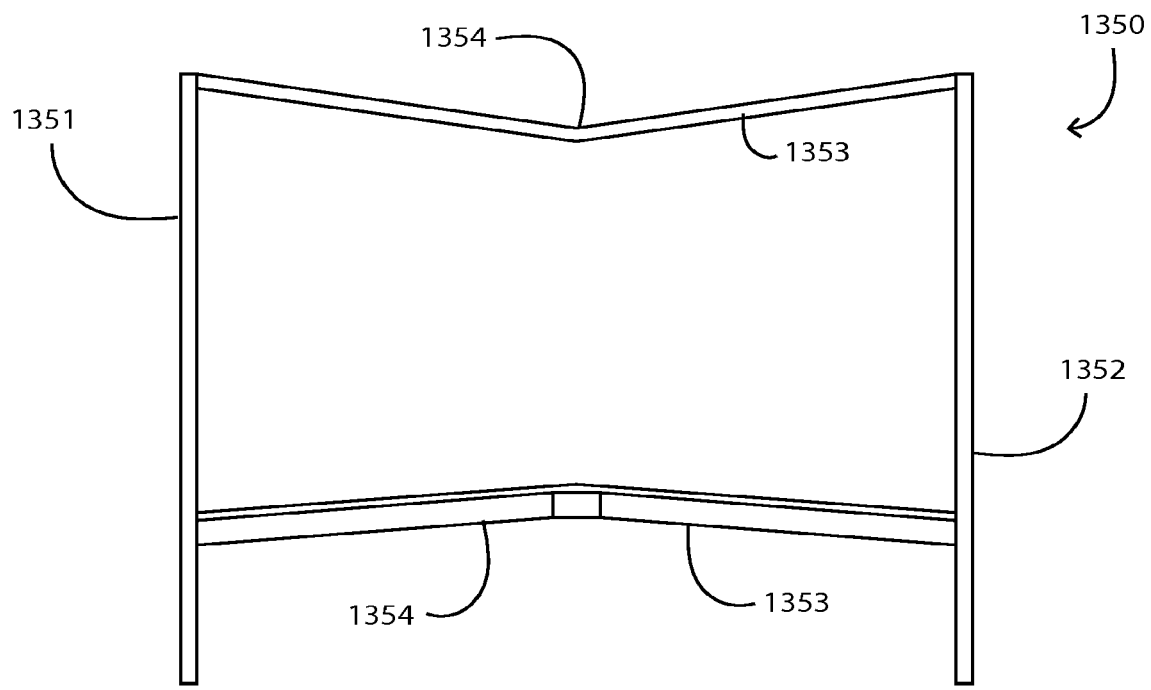
FIG. 42 is an end view showing a frame with longitudinal struts extending between the ends, the struts being bent to from a shallow V-shape.

Also as noted above, a frame may have distal and proximal rings, but the longitudinal struts may be curved to prevent contact with the conduit. Similarly, they may be tapered inwards to avoid this contact. Referring to FIG. 42, a frame 1350 has a distal end 1351, proximal end 1352, and commissures 1353 in between. The commissures 1353 have a smaller or reducing diameter between the distal and proximal ends, with bends 1354 between the ends, each commissure having a shallow V-shape.

Also as noted above, in various embodiments the guide has structural integrity to position and maintain the coaptation assist valve. The guide may comprise a steerable catheter, such as that with a pull wire, which applies tension to at least one eccentric location on the catheter, bending it in that direction. The pull wire may also only act over part of the length of the catheter. In one embodiment, the pull wire is attached to another tube, limiting the length of the catheter that is steered.

Figure 43:
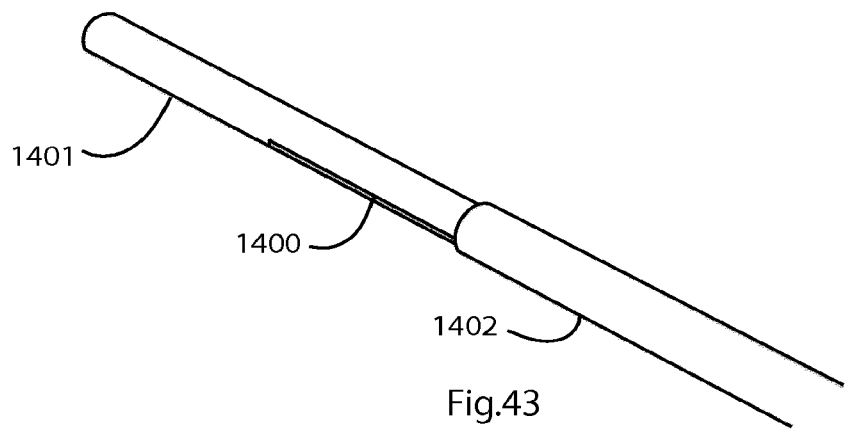
FIG. 43 is a perspective view showing a pull wire extending from an actuator tube and connected to a steerable section of another tube, such that it bends the steerable section upon pulling of the actuation tube proximally.

Referring to FIG. 43 a support has a pull wire 1400 connected to the distal end of a steerable section 1401, and it exits an activation tube 1402 and is connected to the activation tube 1402. Pulling the activation tube 1402 proximally steers the steering section 1401 only, rather than having the pull wire steer over the whole catheter length.

Figure 44:
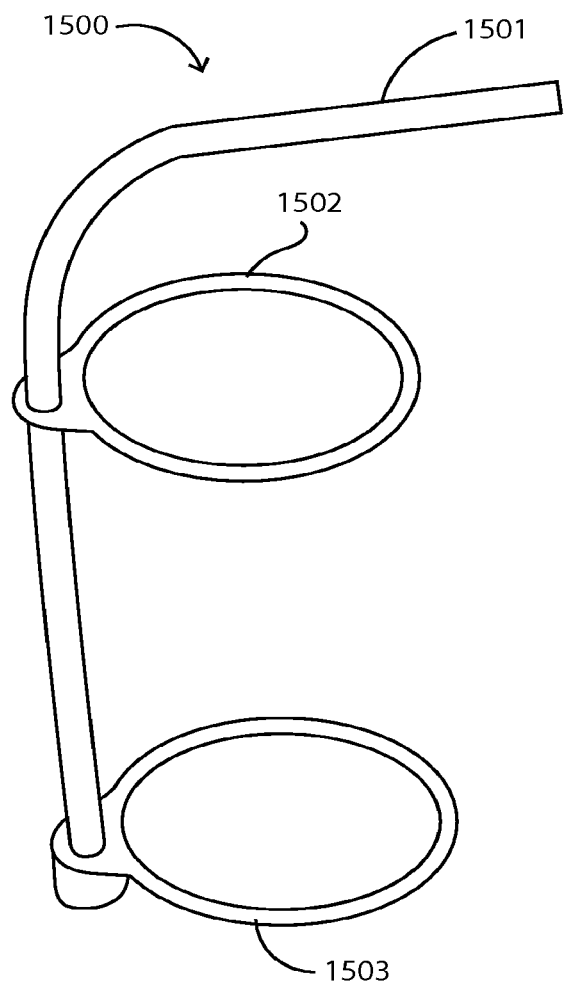
FIG. 44 is a perspective view showing a support with a rail and proximal and distal hoops secured directly to the rail, so that the rail is not central to the conduit.

Referring to FIG. 44 the coaptation assist valve may be connected to the support by direct connections to the distal and proximal structures. This drawing shows a device 1500 having a conduit (not shown) with a support rail 1501 and proximal and distal hoops 1502 and 1503 directly connected to the rail. Hence the rail is not central, rather being at the radial outermost location of the device.

Figure 45:
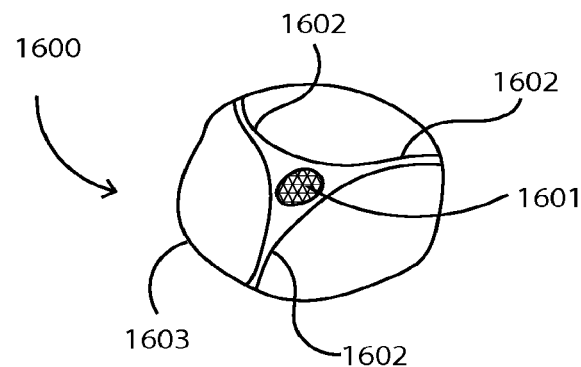
FIG. 45 is an end view of a coaptation assist valve in which the prosthetic valve leaflets are slightly too short and narrow and do not contact the central support.

Referring to FIG. 45, in an alternative coaptation assist valve 1600, in a conduit 1603 valve leaflets 1602 may be configured to coapt with each other but to leave a central hole/core 1601 which does not prevent systolic flow. Where there is a support rail through the valve, this can ensure that the support rail does not coapt with the prosthetic valve leaflets. This can limit or prevent contact between the leaflets and the support rail. Modifications may be made to the support at or near the leaflets to minimise leaks through the valve, such as triangular elements.

The prosthetic valves shown in the above embodiments are prosthetic tissue valves, but other types of valves may also be used such as mechanical valve, ball valve, tilting disc, iris valve, Nitinol leaflets, disc valve for example.

Figure 47:
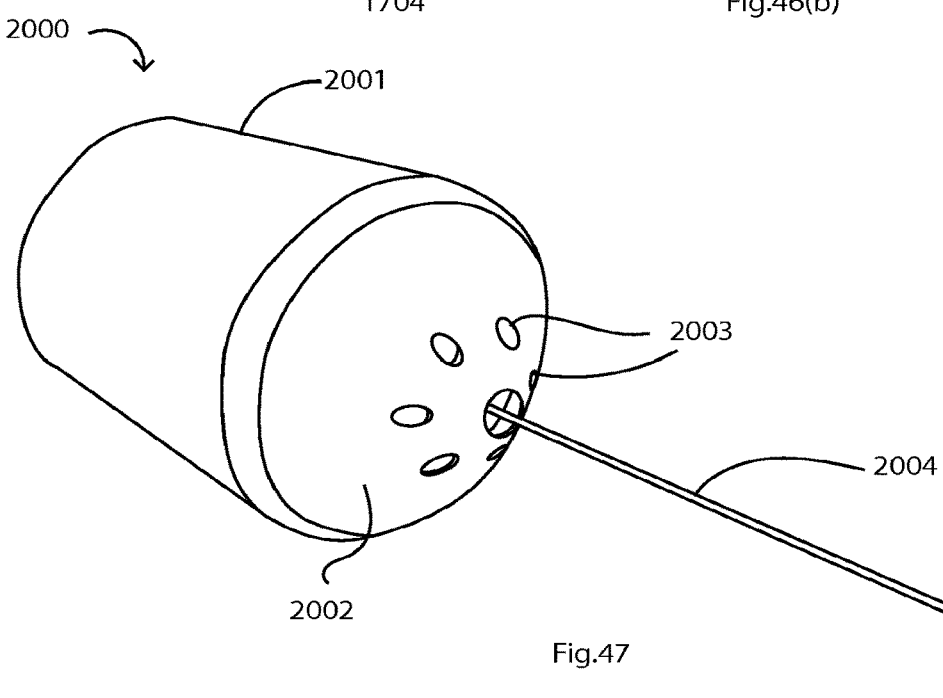
FIG. 47 is a perspective view of an alternative coaptation assist valve with fenestrations.

Referring to FIG. 47 an alternative device 2000 has a parachute-like coaptation assist member having a side wall 2001 and a proximal end 2002, mounted to a support rail 2004. The member 2001/2002 expands during systole and collapses during diastole. In use, the native leaflets provide the valving function, blood flowing around the device 2000. Fenestrations 2003 allow some regurgitant flow during systole, which can limit blood stasis and thrombosis, while significantly reducing regurgitation of the native valve. This member can be attached to the support by one or more tethers or fixed directly to the support. In other embodiments, the device has more rigidity such that the member doesn't expand or collapse during the cardiac cycle.

Temporary treatment of mitral/tricuspid regurgitation would be very useful in some circumstances to assess the cardiac response to reduction in regurgitation. This may be used as an indicator towards the decision to intervene further, as a diagnostic or therapeutic tool. As such, a device of any embodiment may be used as a temporary treatment device, having any suitable components of the therapeutic device of the above embodiments. For example, instead of a coaptation assist valve the device may have a coaptation member which may comprise a balloon or a spacer. The support may include a guide, preferably with sufficient stiffness to maintain the position of the coaptation member. Also, the device may comprise a stabilisation element of any embodiment.

It will be appreciated that the device of various embodiments provides many advantageous features in use arising from the use of a conduit with a flexible side wall with a coaption surface. The device is adapted to primarily act as a flexible conduit. In this case the device may be for treating regurgitation of a native heart valve, the device comprising in one example: a conduit configured to reside across a native heart valve, the conduit having a lumen or channel and a flexible sidewall for coapting with leaflets of the native heart valve, a prosthetic valve mounted within the lumen; and a support.

Such a device may have one or more of the following features:

The flexible sidewall is configured to provide a compliant surface for coapting with leaflets of the native heart valve.

The conduit has distal and proximal ends and further comprises a structural support disposed at each of the distal and proximal ends.

The prosthetic valve comprises one or more prosthetic leaflets mounted within the lumen.

The prosthetic leaflets are cup-shaped.

The structural support at the distal end comprises a distal ring affixed to a distal end of the flexible sidewall.

A structural support at the proximal end comprises a proximal ring affixed to a proximal end of the flexible sidewall.

The structural support at the proximal end further comprises at least one connector extending at least partially radially and that connects to the support rail.

The device has at least one connector which is flexible and allows radial movement of the conduit relative to the support rail.

The device has at least one connector which comprises a tether.

The support is a rail configured to suspend the conduit across the native heart valve.

The device comprises a guide disposed on the support rail, and the guide may be steerable and/or lockable.

The device has a biasing element arranged to bias at least part of the support rail within a patient's vascular system.

The conduit is connected to the support rail at or near the distal end.

The device has a support structure at the distal end which is connected to the support rail.

The prosthetic valve, when open, is configured to allow blood flow through the lumen of the conduit.

The support rail extends through the prosthetic valve and through the lumen of the conduit.

A guide operatively associated with the support rail.

Suspended Therapeutic Element Aspect

In various other embodiments we describe a device which has a therapeutic element which is suspended across a native heart valve using a support of any type described above for use with a therapeutic valve device. Many applications would benefit from the fact that the conduit is suspended by use of cantilever force. Instead of a coaptation assist valve there may be a therapeutic element such as a balloon, a spacer member, or a filled spacer.

In this specification, where the word "suspended" or "suspend" is used it means that the therapeutic element is supported in a cantilevered manner without being fixed locally to patient tissue (such as a ventricle wall).

In various embodiments, preferably the device comprises a support rail configured to suspend the conduit across the native heart valve without anchoring of the support rail to an annulus of the native heart valve or atrial or ventricular tissue adjacent to the native heart valve.

In the drawings referred to above, the coaptation assist valve may be replaced by the therapeutic element which is supported.

Such a device may have one or more of the following features:

The sidewall provides a compliant surface for coapting with leaflets of the native heart valve.

The conduit has distal and proximal ends and further comprises a structural support disposed at each of the distal and proximal ends.

There may be a prosthetic valve which comprises one or more prosthetic leaflets mounted within a lumen. Alternatively, instead of a prosthetic valve there may be mechanical valve, or iris valve.

Where there is a prosthetic valve the prosthetic leaflets may be cup-shaped.

The structural support at the distal end comprises a distal ring affixed to a distal end of the sidewall.

The structural support at the proximal end comprises a proximal ring affixed to a proximal end of the sidewall.

The structural support at the proximal end further comprises at least one connector extending at least partially radially that connects to the support rail.

At least one connector is flexible and allows radial movement of the conduit relative to the support rail.

The at least one connector comprises a tether.

There is a guide disposed on the support rail.

The guide is steerable and/or lockable.

The device further comprises a biasing or stabilisation element arranged to bias at least part of the support within a patient's vascular system.

The conduit is connected to the support at or near the distal end.

The proximal end of the guide is configured to be implanted subcutaneously.

The support is configured to suspend the conduit across the native heart valve without anchoring the device to the native heart valve, or atrial or ventricular tissue.

The support is configured to suspend the conduit across the native heart valve without anchoring the device to any heart tissue.

The support is operatively associated with a guide.

The support rail is disposed within the guide.

Distal and Proximal Structures

In other aspects devices of various embodiments have a conduit with a sidewall with a native leaflet coaptation surface and a structure which is mounted to a support. There may or may not be a prosthetic valve within the conduit. If not, there may be a balloon, spacer member, filled spacer. Such a device may have one or more of the following features:

- The sidewall comprises a flexible material that provides a compliant surface for coapting with the leaflets of the native heart valve.
- The sidewall is unsupported between the distal end and the proximal end.
- The prosthetic valve comprises one or more prosthetic leaflets mounted within the lumen, and the prosthetic leaflets may be cup-shaped.
- The structural support at the distal end comprises a distal ring, and/or at the proximal end comprises a proximal ring, and the device may have at least one connector extending at least partially radially to couple with the proximal ring to the support rail. At least one connector may be flexible to allow radial movement of the conduit relative to the support rail. At least one connector may comprise a tether.
- The device may have a guide disposed on the support rail, and the guide may be steerable and/or lockable.
- The device may comprise a biasing element arranged to bias at least part of the support rail within a patient's vascular system.
- The distal ring may be coupled to the support rail at or near the distal end.
- The support rail may have a proximal end configured for subcutaneous implantation.
- The device may have a structural support at the distal end and a structural support at the proximal end, and these supports may be coupled to form a single unit.
- The prosthetic valve, when open, may be configured to allow blood flow through the lumen of the conduit.
- The support rail may extend through the prosthetic valve and through the lumen of the conduit.
- A guide operatively associated with the support rail Lockable Rail Devices of various embodiments may have a support which is lockable, but there may be a different therapeutic element at the distal end of the support instead of a coaptation assist valve. Such an element may be a balloon, spacer member, or a filled spacer for example. Any of the drawings referred to above which has a support which is lockable illustrate the lockable rail features for such a device.

Such a device may have one or more of the following features:

- The sidewall is flexible and provides a compliant surface for coapting with leaflets of the native heart valve.
- The conduit has distal and proximal ends and further comprises a structural support disposed at each of the distal and proximal ends.
- The prosthetic valve comprises one or more prosthetic leaflets mounted within the lumen, and the prosthetic leaflets may be cup-shaped.
- The structural support at the distal end comprises a distal ring affixed to a distal end of the sidewall.
- The structural support at the proximal end comprises a proximal ring affixed to a proximal end of the sidewall.
- A connector extends at least partially radially that connects the proximal ring to the support rail.
- At least one connector is flexible and allows radial movement of the conduit relative to the support rail.
- At least one connector comprises a tether.
- The device comprises a stent disposed on the guide, the stent configured for deployment in the superior vena cava or right atrium to stabilize the guide and the support rail.
- The guide is steerable.
- The device comprises a biasing element arranged to bias at least part of the guide or the support rail within a patient's vascular system.
- The conduit is connected to the support rail at or near the distal end.
- The proximal end of the guide is configured to be implanted subcutaneously.
- The support rail is disposed within the guide.
- The distal portion of the support rail extends beyond the distal end of the guide to suspend the conduit across the native heart valve.
- The device further comprises a lock for rigidly engaging the guide to the support rail, and the lock may rigidly engage the proximal end of the guide to the proximal portion of the support rail.
- The prosthetic valve, when open, is configured to allow blood flow through the lumen of the conduit.
- The support rail extends through the prosthetic valve and through the lumen of the conduit.

Coaptation Member

In various embodiments the device may have, instead of a coaptation assist valve with a prosthetic valve, a coaptation member such as balloon, spacer member, filled spacer. The coaptation member is configured to reside across a native heart valve so that the sidewall coapts with leaflets of the native heart valve and a support is coupled to the coaptation member, and the support may have a guide operatively associated with the support. Such a device may have one or more of the following features:

- The sidewall comprises a flexible material that provides a compliant surface for coapting with the leaflets of the native heart valve.
- The device may have a guide disposed on the support rail, and the guide may be steerable and/or lockable.
- The device may comprise a biasing element arranged to bias at least part of the support rail within a patient's vascular system.
- The support rail may have a proximal end configured for subcutaneous implantation.
- The support rail may extend through the coaptation member.
- A guide operatively associated with the support rail.
- The guide is steerable by manipulating a shape with a pre-formed bend 1102.
- The coaptation member is extensible over the rail using telescope elements.

FIG. 37 shows a coaptation member that can be steered into the right direction, the then extended out further in relation to the bend. It also shows telescopic tubing for this. The element which is at the distal end need not necessarily be a coaptation assist valve.

Support with Steerable Guide

As shown for example in FIGS. 37(*a*) to (*e*), in other aspects a device of a different type may be mounted to a support with a steerable guide of any type described above. Such a support is advantageous for positioning a therapeutic element.

The guide preferably has a shaped bend and a stiffer member for controlling the shape of the shaped bend.

Examples of where this would be used are placements of stents/pacemakers, implants, therapeutic injections and tattooing, ablation catheters. Such a device may have one or more of the following features:

The guide is steerable and/or lockable.
The guide is steerable by changing a shape with a pre-formed bend (1102).
The guide (1100) comprises telescopic tubing (1102).
The telescopic tubing (1102) is around a still rod (1102), which may extend into a rigid tube (1101).
The element comprises rigid telescopic elements to enhance stability on the guide.
The guide also comprising a biasing element as claimed in claim 87, wherein the biasing element (371) is arranged to bias the guide (372) towards a vessel wall, limiting lateral movement.
The guide may be configured to vary curvature of an elongate support in a medical device.
The guide may have a pre-set bend to guide position and/or orientation of the support (10).
The guide may be (331) steerable and/or lockable.
The guide may be steerable by straightening a shape with a pre-formed bend (1102).
The guide (1100) may comprise telescopic tubing (1102).
The telescopic tubing (1102) may be around a still rod (1102), which may extend into a rigid tube (1101).
The support may include an element (1102) that can be advanced relative to a bend in the guide to position the support relative to the bend.
The element may comprise rigid telescopic elements to enhance stability on the guide.
The support (10) may have variable properties along its length.
The guide (331) may have variable properties along its length.

Stabilisation Element

In various embodiments we describe a medical device for deployment in a blood vessel and having an elongate support with a rail. The support also includes a stabilising element for holding the support rail at a desired radial position in the blood vessel, thereby biasing the support proximally and/or distally of the stabilisation element towards that radial location.

The element (371) may be arranged to bias the guide (372) towards a vessel wall, limiting lateral movement.

The element (371) may comprise shaped wire. The element (371) may comprise a stent (1120) or stent-like structure, and such a structure may optionally include a tube to receive a support (1100).

The element (371) is arranged to limit lateral, axial and/or rotational movement, and may retain the support (1220) in a central, axial, position or another position between axial and an outer position at the circumference of the stent.

Methods of Use in Treatment

The device in its various embodiments is suitable for delivery of a coaptation assist device for repair of the mitral and tricuspid valves. The coaptation body is delivery in a collapsed, low profile configuration and delivered to the treatment site. A stabilisation element is deployed to stabilise movement of the device and the coaptation body is fine positioned across the native valve. The device is fixed in place relative to the anatomy using a fixation element, the handle detached. Excess length can be detached.

Advantages

The following are some advantages of devices of various embodiments.

In many examples, the therapeutic element is suspended by cantilever action, thereby allowing it to be optimally positioned across the native heart valve, and in some cases even self-orientating. This is done in a minimally invasive manner because there is no fixation to heart tissue.

Uses the native valve for coaption; valve repair rather than valve replacement.

Allows unidirectional flow through the conduit; this causes a reduction in valve regurgitation while causing minimal obstruction during flows.

Compliant conduit to minimise potential trauma if in contact with native structure Structure of the coaptation surface achieved through pressure rather than frame structure Equal pressures on two coapting surfaces so that the coaptation surface deforms to fill the regurgitant orifice area.

The coaptation surface is free to respond to cardiac motion and optimally position/orientation itself within the native valve.

Tethers, connecting the valve element to the support structure are flexible to facilitate this response to cardiac motion.

Coaptation assist valve is supported through distal and proximal support structures with a central support member.

Long valve element allows for the support to run through the valve element without reducing valve function, supporting a long coaptation zone for the prosthetic valve.

Valve element may be sheet fixed to the internal surface of the coaptation surface with individual leaflets created by fixation points.

The invention is not limited to the embodiments described but may be varied in construction and detail. In various embodiments components of the device may be used with other devices. For example, the biasing element such as a stent as described may be used with a support for any other purpose such as support of a therapeutic valve for any other part of the heart, or for a therapeutic spacer or balloon for assisting coaptation, or any other coaptation assist element for valve repair.

The guide (fixed bend or steerable) may be used for guiding a support for any other device, such as a therapeutic spacer or balloon for valve repair, or any other coaptation assist element for valve repair.

What is claimed:

1. A heart valve therapeutic device for placement across a patient's native heart valve, the heart valve therapeutic device comprising:
   a coaptation assist element comprising a side wall between a proximal end and a distal end, the side wall having an external surface configured to coapt with native leaflets of the native heart valve;
   a support comprising a guide tube and an elongate support rail configured to be disposed within the guide tube, the coaptation assist element coupled to the support such that the coaptation assist element is configured to reside across the native heart valve;
   a stabilization element comprising a stent coupled to the support configured to retain the support in a position in the patient; and
   a tube coupled to and extending within the stabilization element, the tube configured to receive the support.

2. The heart valve therapeutic device of claim 1, wherein the coaptation assist element has a tubular shape.

3. The heart valve therapeutic device of claim 1, wherein the support comprises at least one connector connecting the coaptation assist element to the elongate support rail.

4. The heart valve therapeutic device of claim 1, wherein the support is configured to suspend the coaptation assist element across the native heart valve without anchoring of the device to an annulus of the native heart valve or atrial or ventricular tissue adjacent to the native heart valve.

5. The heart valve therapeutic device of claim 1, wherein the support is configured to extend percutaneously into a blood vessel coupled to the heart.

6. The heart valve therapeutic device of claim 1, wherein the support has a pre-set bend.

7. The heart valve therapeutic device of claim 1, wherein the support is steerable and has a pre-set bend.

8. The heart valve therapeutic device of claim 1, wherein the support is steerable and lockable.

9. The heart valve therapeutic device of claim 1, wherein a distal portion of the elongate support rail extends distally of the distal end of the guide tube to suspend the coaptation assist element across the native heart valve in use.

10. The heart valve therapeutic device of claim 1, wherein the support comprises a lock configured to engage the guide tube to the support rail.

11. The heart valve therapeutic device of claim 1, wherein the guide tube comprises telescopic tubing for advancing or retracting the coaptation assist element.

12. The heart valve therapeutic device of claim 1, wherein the stabilization element is configured to hold the support at a particular radial location, thereby biasing at least part of the support towards the radial location.

13. The heart valve therapeutic device of claim 1, wherein the stent is configured to engage the wall of a blood vessel.

14. The heart valve therapeutic device of claim 1, further comprising a fixation element configured to limit movement of the coaptation assist element, wherein the fixation element comprises a collet.

15. The heart valve therapeutic device of claim 1, wherein the side wall comprises flexible material that provides the external surface.

16. The heart valve therapeutic device of claim 15, wherein the flexible material is expandable to provide a compliant surface for coapting with the native leaflets.

17. The heart valve therapeutic device of claim 1, wherein the coaptation assist element comprises a conduit configured to allow blood flow through a channel within the conduit.

18. The heart valve therapeutic device of claim 17, wherein the coaptation assist element further comprises a prosthetic valve mounted within the conduit.

19. The heart valve therapeutic device of claim 18, wherein the prosthetic valve is configured to allow blood flow through the conduit substantially in one direction only, and the prosthetic valve is configured to allow diastolic blood flow and to prevent systolic blood flow.

20. The heart valve therapeutic device of claim 18, wherein the prosthetic valve is positioned at proximal end of the coaptation assist element.

21. The heart valve therapeutic device of claim 18, wherein the prosthetic valve comprises a plurality of prosthetic leaflets mounted within the conduit, and wherein the leaflets include the same material as at least part of the side wall.

22. The heart valve therapeutic device of claim 1, wherein the coaptation assist element comprises a distal structure and a proximal structure configured to support the distal and proximal ends of the coaptation assist element.

23. The heart valve therapeutic device of claim 22, wherein the distal structure comprises a ring.

24. The heart valve therapeutic device of claim 22, wherein the proximal structure comprises a ring.

25. The heart valve therapeutic device of claim 22, wherein the distal structure and the proximal structure are included in an integral frame.

26. The heart valve therapeutic device of claim 22, wherein the distal structure or the proximal structure or both comprise spokes connected to the support.

27. The heart valve therapeutic device of claim 1, wherein the support extends through the coaptation assist element.

28. The heart valve therapeutic device of claim 1, wherein the support has a proximal end configured for subcutaneous implantation.

29. A method for placing a heart valve therapeutic device across a patient's native heart valve, the method comprising:
  advancing a coaptation assist element coupled to a support to the patient's native heart valve, the coaptation assist element comprising a side wall between a proximal end and a distal end, the support comprising a guide tube and an elongate support rail disposed within the guide tube; and
  anchoring a stabilization element comprising a stent coupled to the support via a tube extending within the stabilization element configured to receive the support to retain the support in a position in the patient such that the coaptation assist element resides across the native heart valve and native leaflets of the native heart valve coapt against an external surface of the side wall when the native leaflets close during the cardiac cycle.

* * * * *